US012584155B2

(12) United States Patent
Piotrowski et al.

(10) Patent No.: US 12,584,155 B2
(45) Date of Patent: Mar. 24, 2026

(54) METHOD AND KIT FOR ASSEMBLY OF MULTIPLE DNA FRAGMENTS AT ROOM TEMPERATURE

(71) Applicant: Universitetet I Tromsø—Norges Arktiske Universitet, Langnes (NO)

(72) Inventors: Yvonne Piotrowski, Tromsø (NO); Atle Noralf Larsen, Kvaløya (NO)

(73) Assignee: UNIVERSITETET I TROMSØ—NORGES ARKTISKE UNIVERSITET, Lagnes (NO)

( * ) Notice: Subject to any disclaimer, the term of this patent is extended or adjusted under 35 U.S.C. 154(b) by 1028 days.

(21) Appl. No.: 17/765,710

(22) PCT Filed: Oct. 1, 2020

(86) PCT No.: PCT/EP2020/077549
§ 371 (c)(1),
(2) Date: Mar. 31, 2022

(87) PCT Pub. No.: WO2021/064115
PCT Pub. Date: Apr. 8, 2021

(65) Prior Publication Data
US 2023/0220435 A1 Jul. 13, 2023

(30) Foreign Application Priority Data
Oct. 1, 2019 (EP) .................................... 19200792

(51) Int. Cl.
*C12P 19/34* (2006.01)
*C12N 9/12* (2006.01)
(52) U.S. Cl.
CPC ............ *C12P 19/34* (2013.01); *C12N 9/1252* (2013.01); *C12Y 207/07007* (2013.01)
(58) Field of Classification Search
CPC ...................... C12N 9/1252; C12Y 207/07007
See application file for complete search history.

(56) References Cited

FOREIGN PATENT DOCUMENTS

| | | | |
|---|---|---|---|
| EP | 1915446 B1 | 4/2008 | |
| EP | 1929012 B1 | 6/2008 | |
| EP | 2955227 B1 | 12/2015 | |
| WO | 2007124065 A1 | 11/2007 | |
| WO | 2009103027 A2 | 8/2009 | |
| WO | 2010045326 A1 | 4/2010 | |
| WO | 2016033315 A2 | 3/2016 | |

OTHER PUBLICATIONS

Li, et al.; "SLIC: a method for sequence and ligation independent cloning"; Gene Synthesis, vol. 852; 2012; pp. 51-59.

Cavicchioli, R. et al.; "Biotechnological uses of enzymes from psychrophiles: Enzymes from psychrophiles"; Microbial Biotechnology, vol. 4, Issue No. 4; 2011; pp. 449-460.
Cohen, et al.; "Construction of Biologically Functional Bacterial Plasmids In Vitro"; PNAS, vol. 70, Issue No. 11; 1973; pp. 3240-3244.
DATABASE geneseq [Online] Nov. 26, 2014 (Nov. 26, 2014), "DNA polymerase"; retrieved from EBI Accession No. UNIPROT:A0A090IAP3.
DATABASE geneseq [Online] Jan. 31, 2018 (Jan. 31, 2018), "DNA polymerase I"; retrieved from EBI Accession No. UNIPROT:A0A2G2J1S6.
DATABASE geneseq [Online] Jun. 8, 2016 (Jun. 8, 2016), "DNA polymerase"; retrieved from EBI Accession No. UNIPROT:A0A137S9V1.
European Search Report for European Application 19200792.0 [PCT/EP2020/077549] dated Apr. 9, 2020; 14 pages.
International Search Report and Written Opinion for International Application PCT/EP2020/077549; International Filing Date: Oct. 1, 2020; Date of Mailing: Dec. 1, 2020; 21 pages.
Under, et al.; "'Winter ulcer' in the Atlantic salmon *Salmo salar*. Pathological and bacteriological investigations and transmission experiments"; Disease of Aquatic Organisms, vol. 23, Issue No. 23; 1995; pp. 39-49.
Mcwilliam, et al.; "Analysis Tool Web Services from the EMBL-EBI"; Nucleic Acids Research, vol. 41; 2013; pp. W597-W600.
Piotrowski, Y. et al.; "Characterization and engineering of a DNA polymerase reveals a single amino-acid substitution in the fingers subdomain to increase strand-displacement activity of A-family prokaryotic DNA polymerases"; BMC Molecular and Cell Biology, vol. 20, Article No. 31; 2019; pp. 1-11.
Sievers, F. et al.; "Clustal Omega for making accurate alignments of many protein sequences"; Protein Science, vol. 27; 2018; pp. 135-145.
Simon, C. et al.; "Rapid Identification of Genes Encoding DNA Polymerases by Function-Based Screening of Metagenomic Libraries Derived from Glacial Ice"; Applied and Environmental Biology, vol. 75, Issue No. 9; 2009; pp. 2964-2968.
Singh, K. et al.; "Participation of the Fingers Subdomain of *Escherichia coli* DNA Polymerase I in the Strand Displacement Synthesis of DNA"; Journal of Biological Chemistry, vol. 282, Issue No. 14; 2007; pp. 10594-10604.
Summerer, D.; "DNA Polymerase Profiling"; Methods of Molecular Biology, vol. 429; 2008; pp. 225-235; DOI: 10.1007/978-1-60327-040-3_16.

*Primary Examiner* — Robert J Yamasaki
(74) *Attorney, Agent, or Firm* — Karen A. LeCuyer; DeWitt LLP

(57) ABSTRACT

The present invention relates to recombinant DNA technology, in particular to methods for assembling two or more double stranded (ds) nucleic acid molecules with overlapping terminal sequences. In particular, the present invention relates to the use of a thermolabile DNA polymerase II derived 3'-5' exonuclease isolated from *Moritella viscoa* and a thermolabile DNA polymerase I of marine origin in multi DNA assembly processes.

13 Claims, 11 Drawing Sheets
Specification includes a Sequence Listing.

A        DNA pol I (MG pol I)

B
DNA polymerase I variants

```
         440          450          460          470          480
SSVRRRAHAI  HFSIIYGISA  FGLAHHLGIS  RIEAKEYIDS  YFEKFPGIKT
```

S449A/F451A (AAA)
A450D (SDF)
A450D/F451A (SDA)
S449A/A450D (ADF)
S449A/A450D/F451A (ADA)
R521A (R521A)

FIG. 8

A                    DNA pol II

B
DNA polymerase II variants
SM1 → D442A
SM2 → D568A
DM1 → D442A/D568A
SM4 → D442E
SM5 → D568E

FIG. 12

METHOD AND KIT FOR ASSEMBLY OF MULTIPLE DNA FRAGMENTS AT ROOM TEMPERATURE

CROSS REFERENCE TO RELATED APPLICATIONS

This application is a National Stage application of PCT/EP2020/077549, filed Oct. 1, 2020, which claims priority to European Patent Application No. 19200792.0, filed Oct. 1, 2019, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Sep. 7, 2022 is named "OSA0071US Replacement Sequence List_ST25" and is 107,954 bytes in size.

FIELD OF INVENTION

The present invention relates to recombinant DNA technology, in particular to methods for assembling two or more double stranded (ds) nucleic acid molecules with overlapping terminal sequences. In particular, the present invention relates to the use of a thermolabile DNA polymerase II derived 3'-5' exonuclease isolated from *Moritella viscoa* and a thermolabile DNA polymerase I of marine origin in multi DNA assembly processes.

BACKGROUND OF THE INVENTION

Synthetic biology is a rapidly evolving field and is heralded as a possible solution for the challenges in future bio-economy and bioenergy. The ultimate vision of synthetic biology is to create new biological operating systems of cells that predictably can carry out useful tasks. One of the key steps in a synthetic biology pipeline is the assembly of DNA fragments into larger functional constructs often involving multiple assemblies.

Since the cloning of individual genes into replicating plasmid, and the introduction thereof in host cell as reported in Cohen, Chang, Boyer and Helling in 1973 (Proc. Natl. Acad Sci, 70(11), pp. 3240-3244, numerous cloning techniques have become available, also enabling the introduction of more than one nucleic acid molecule into appropriate vectors.

For example, Li and Elledge describes in WO2007/124065 an in vitro homologous recombination method that are sequence and ligase independent (SLIC), wherein dsDNA molecules are assembled by combining exonuclease treated target DNAs with homologous overhangs that are annealed, and wherein the missing nucleotides in the annealed region is filled in by the appropriate host cell after transformation.

Reference is also made to Gene Synthesis, Methods and Protocols, Methods in Molecular biology, 2012, vol. 852, pp 51-59 disclosing a SLIC protocol for production of recombinant DNA wherein target dsDNA(s) is inserted into a vector of choice using the exonuclease activity of T4 DNA polymerase (in absence of dNTPs) to produce single stranded overhangs of the dsDNA to be combined, followed by annealing and ligase treatment of the annealed product. T4 DNA polymerase has very strong exonuclease activity, thus timing of the reaction is very important. Furthermore, the presence of dNTP would most likely prevent the exonuclease reaction (because polymerase reaction would be preferred). It follows that dsDNA to be assembled need to be purified, i.e. freed from dNTPs, after the PCR. This is quite demanding for the assembly of several and larger fragments.

Other methods based on homolog recombination is disclosed in e.g. EP1929012 disclosing a homologue recombination method wherein dsDNA molecules are assembled after being treated with a 3'-5' exonuclease that produces overhang, followed by annealing, contacting the annealed products with a DNA polymerase, and finally sealing the remining nicks using a ligase, and wherein the process is performed in the presence of a crowding agent (such as PEG).

In EP1915446A1, a method is disclosed wherein dsDNA molecules of interest are assembled utilizing a non-processive 5' exonuclease, a non-strand displacing DNA polymerase and a ligase. In the method disclosed in EP1915446, the annealing process is carried out at elevated temperatures (45 to 60° C.) and using a ssDNA binding protein.

Yet another in vitro homolog recombination method is disclosed in EP2255013, wherein a one vessel process is presented that is inter alia carried out at isothermal conditions of about 45° C. to 60° C.

A current bottleneck is however the lack of a robust room-temperature method to do multiple DNA assemblies without time-consuming manual treatment steps. A new DNA assembly method able to bypass the current hurdles is therefore highly desired.

In ordered to achieve this the inventors have identified two polymerases of marine origin, one DNA polymerase I (MG pol I) and one DNA polymerase II enzyme (MV pol II) which have been modified in order to gain enzymatic properties suitable for DNA amplification methods and DNA assembly processes performed at room temperatures and without any time consuming manual steps.

The present inventors have identified a DNA polymerase I (MG pol I) by metagenomic analysis of marine environmental samples collected in the marine artic area around Svalbard. Unlike other many known DNA pol I, the present isolated MG pol I is intrinsically heat labile which renders the enzymes specifically useful in molecular biology processes, such as in a variety of DNA amplification processes and DNA assembly processes. For example, the present MG pol I polymerase is rapidly and irreversible inactivated at temperatures above 25° C., such as at temperatures above about 30° C., resulting in no need for any inactivation step before further handling of a product being subjected to the DNA polymerase of the present invention.

In addition, the present inventors have shown that the present MG pol I exerts a very robust polymerase activity compared with commercially available DNA polymerases, such as the mesophilic Klenow enzyme from *E. coli* and the thermophilic Bst polymerase originating from *Bacillus stearothermophilus*.

The robust polymerase activity as well as the temperature lability characteristics of the present MG pol I makes it a very useful DNA pol I for a wide range of DNA amplification processes, which can be performed at room-temperature and which avoids the need of an inactivation step.

The present MG pol I furthermore exert 3'-5' exonuclease activity, resulting in proof reading of the replicated DNA molecule.

Piotrowski, Y. et al., Molecular and Cell biology, 2019, page 1-11 and Singh, K. et al., J. of Biological Chemistry, 2007, vol. 282, no. 14, page 10594-10604 disclose mutant DNA polymerases with altered strand displacement activity.

The present inventors have also synthesized modified variants of the MG pol I of the present invention, wherein the strand displacement activity of the DNA polymerase is sufficiently impaired or absent.

The modified MG pol I of the present invention with impaired or lacking strand displacement activity is in particularly useful in recombinant cloning processes, e.g. wherein two or more double stranded nucleic acid molecules with single stranded 5' overhang is assembled.

In particular, a modified DNA polymerase with impaired or lacking strand displacement activity is useful in multiple DNA assembly methods.

Further the DNA polymerase of the present invention is a large fragment DNA polymerase lacking the 5'-3' exonuclease domain and having impaired or lacking strand displacement activity is also in particularly useful in recombinant cloning processes, e.g. wherein two or more double stranded nucleic acid molecules with single stranded 5' overhang is assembled.

Further the DNA polymerase of the present invention is a large fragment DNA polymerase I lacking the 5'-3' exonuclease domain and having impaired or lacking strand displacement activity is also in particularly useful in multiple DNA assembly processes.

A further advantage of the identified MG pol I is that the temperature for optimal activity is around room temperature. A further advantage of the present MG pol I is that when used in DNA amplification or DNA assembly processes, as shown further below, no inactivation step deemed is necessary.

The present inventors have also identified a heat labile DNA polymerase II originating from Moritella viscosa (MV pol II) surprisingly found to have a very strong 3'-5' exonuclease activity in absence of dNTPs. The enzyme of the present invention was identified in a Moritella viscosa strain from farmed Atlantic salmon affected by winter ulcer disease as disclosed further below in the experimental part.

In particular, it was found that the present MV pol II 3'-5' exonuclease is able to bind double stranded DNA molecules and degrade the ends thereof in 3'-5' direction, resulting in 5' overhang in both ends of DNA molecules subjected to the DNA pol derived 3'-5 exonucleases of the present invention.

Furthermore, the identified that the MV pol II of the present invention was also found to have very poor polymerase activity at room temperature. Furthermore, it has been shown to be easily inactivated at temperatures above 25° C., such as above about 30° C., resulting in that the exonuclease activity will cease within a short time, such as e.g. within 5-30 minutes if used at a temperature within the range of 18° C.-25° C.

The combination of 3'-5 exonuclease activity, poor polymerase activity and heat lability renders the MV pol II enzyme useful in molecular cloning, polynucleotide removal and DNA assembly processes as further shown below. Yet an advantage of the present MV pol II, is that the exonuclease activity is active also in presence of dNTPs. dsDNA molecules to be assembled according to the present process need therefore not to be purified, i.e. freed from dNTP left over from the PCR process.

In order to be able to make use of the 3'-5'-exonuclease activity only, the present inventors have also synthesized modified variants of the MV pol II of the present invention, wherein the polymerase activity is sufficiently impaired or absent.

Using the above described MG pol I mutant enzymes lacking strand displacement activity and the MV pol II mutant enzymes having 3'-5' exonuclease activity but lacking polymerase activity the inventors have developed an efficient DNA assembly method suitable for assembly of multiple DNA fragments at room temperature. The assembly process is shown in FIG. 1 and example 1.

SUMMARY OF THE INVENTION

The present invention provides in a first aspect an in vitro process for assembly of two or more double-stranded (ds) DNA molecules wherein the assembly process takes place at room temperature and wherein said process comprises the steps of:

(a) providing two or more linearized dsDNA molecules to be assembled, whereby the DNA molecules to be assembled share a region of sequence identity at their terminal regions such that the distal region of the one DNA molecule and the proximal region of the second DNA molecule share sequence identity;

(b) contacting the two or more DNA molecules to be assembled from step (a) with a thermolabile/heat labile of 3'-5' exonuclease that generates 5' single stranded overhangs at the terminal regions of the dsDNA molecules;

(c) incubating the DNA molecules generated in step (b) under conditions whereby the overlapping overhanging regions of the two or more DNA molecules anneal; and (d) contacting the annealed assembled DNA molecules of step (c) with a thermolabile/heat labile DNA polymerase I (pol I) that is substantially without strand-displacement activity under conditions whereby the remining single-stranded gaps between the annealed fragments are filled in by the pol I enzyme thereby assembling the two or more dsDNA molecules.

According to one aspect of the above process, the process takes place at any temperature from about 18° C. to about 25° C. According to yet another aspect of the above process, said takes place at a constant temperature about 25° C.

According to one aspect of the above process, the thermolabile/heat labile DNA polymerase I (pol I) that is substantially without strand-displacement activity is a large fragment DNA polymerase lacking the N-terminal 5'-3'-exonuclease domain. The time spent to carry out the various steps (a) to (d) of the above process may vary. For example, according to one aspect, the steps (a) to (b) is carried out in about 5 minutes or more. In yet another example, the 3'-5' exonuclease is in contact with the two or more DNA molecules of step (b) for at least 5 minutes; the annealing reaction of step (c) takes place for 15 minutes or more; and the gap-filling reaction of step (d) takes place for 10 minutes or more.

According to yet another aspect of the present process, the single stranded overhangs generated in step (b) are at least 8 bases long. In yet another aspect, the single stranded overhangs generated in step (b) are from about 10 bases to about 40 bases long.

According to yet an aspect of the present invention, a process is provided wherein the 3'-5' exonuclease of step (b) and the DNA pol I of step (d) are irreversible inactivated at temperatures above 25° C., such as at above 30° C.

According to yet another aspect of the present process, the 3'-5' exonuclease enzyme of step (b) is a DNA pol II enzyme that exhibits exonuclease activity in the presence of dNTPs.

Furthermore, according to a further aspect, said enzyme is an enzyme of marine origin.

According to yet another aspect, said enzyme has a reduced, impaired or lacks polymerase activity.

According to yet another aspect of the present invention, the 3'-5' exonuclease of step (b) is a DNA polymerase II derived 3'-5' exonuclease is from the bacterium *Moritella viscosa*.

In one embodiment according to any of the above aspects the isolated DNA polymerase II derived 3'-5' exonuclease or an enzymatically active fragment thereof is a DNA polymerase derived 3'-5' exonuclease selected from a group of DNA polymerases derived 3'-5' exonucleases comprising an amino acid sequence wherein the amino acid in position 442 is Ala;

the amino acid in position 568 is Ala;

the amino acid in position 442 is Glu;

the amino acid in position 568 is Glu;

the amino acid in position 442 and 568 is Ala; and the amino acid in position 445 is Arg and wherein the numbering is according to amino acid sequence of SEQ ID No. 1.

The DNA polymerase derived 3'-5' exonuclease according to the above embodiment is a DNA polymerase II derived 3'-5' exonuclease substantially without polymerase activity and wherein said enzyme is irreversibly inactivated at temperatures above 25° C., such as at temperatures above about 30° C.

According to a further aspect, said 3'-5' exonuclease is a DNA polymerase II derived 3'-5' exonuclease enzyme or an enzymatically active fragment thereof wherein the enzyme or the enzymatically active fragment thereof comprising an amino acid sequences having at least about 60% sequence identity over the entire length of the sequence such as at least, 70%, 75%, 80%, 85%, 90%, 95%, 96%, 97%, 98%, or 99% sequence identity over the entire length of the sequence of any one of the sequences selected from the group consisting of SEQ ID No. 12, SEQ ID No. 13, SEQ ID No. 14, SEQ ID No. 15, SEQ ID No. 16 and SEQ ID No. 17 providing that the amino acid in position 442 in SEQ ID No. 12 is Ala;

the amino acid in position 568 in SEQ ID No. 13 is Ala;

the amino acid in position 442 in SEQ ID No. 14 is Glu;

the amino acid in position 568 in SEQ ID No. 15 is Glu;

the amino acid in position 442 and 568 in SEQ ID No. 16 is Ala; and the amino acid in position 445 in SEQ ID No. 17 is Arg and wherein DNA polymerase II derived 3'-5' exonuclease enzyme or the enzymatically active fragment thereof further lacks DNA polymerase activity.

According to yet another aspect, said DNA polymerase II derived 3'-5' exonuclease enzyme or the enzymatically active fragment thereof comprises an amino acid sequences selected from the group consisting of SEQ ID No. 12, SEQ ID No. 13, SEQ ID No. 14, SEQ ID No. 15, SEQ ID No. 16 and SEQ ID No. 17.

According to yet an aspect of the present invention, a process is provided wherein the DNA pol I enzyme of step (d) is a DNA pol I enzyme is substantially without strand-displacement activity. According to a further aspect of the present process, said DNA pol I enzyme is a DNA pol I enzyme having 3'-5' exonuclease activity.

According to yet an aspect of the present invention, a process is provided, wherein the two or more DNA molecules of step (b) are brought in contact with the 3-5' exonuclease in separately vessels or in the same vessel.

According to yet an aspect of the present invention, a process is provided, wherein the dsDNA molecules to be assembled consist of a linearized vector or a transporter construct (such as cosmids) and at least one linearized dsDNA fragment to be inserted into the vector or the transporter construct.

According to yet an aspect of the present invention, assembled dsDNA molecule of step (d) is transformed into a suitable competent host cell.

According to jet another the isolated DNA pol I is a large fragment DNA polymerase I or an enzymatically active fragment thereof wherein the DNA pol I is selected from a group of DNA polymerases comprising an amino acid sequence wherein the amino acid in position 450 is Asp, the amino acids in position 449 and 451 are Ala, the amino acids in position 449 and 450 are Ala and Asp, respectively, the amino acids in position 450 and 451 are Asp and Ala, respectively, the amino acids in position 449, 450 and 451 are Ala, Asp and Ala, respectively, the amino acid in position 521 in SEQ ID No. 8 is Ala and wherein the numbering is according to numbering of the amino acids of SEQ ID No. 1 and wherein the DNA pol I or the enzymatically active fragment thereof further lacks strand-displacement activity and 5'-3' exonuclease activity.

According to yet another aspect of the present invention, the DNA pol I or an enzymatically fragment thereof comprises an amino acid sequence having at least about 60% sequence identity over the entire length of the sequence such as at least, 70%, 75%, 80%, 85%, 90%, 95%, 96%, 97%, 98%, or 99% sequence identity over the entire length of the sequence of any one of the sequences selected from the group consisting of SEQ ID No. 3, SEQ ID No. 4, SEQ ID No. 5, SEQ ID No. 6, SEQ ID No. 7 and SEQ ID No. 8 providing that the amino acid in position 450 in SEQ ID No. 3 is Asp, the amino acids in position 449 and 451 in SEQ ID No. 4 are Ala, the amino acids in position 449 and 450 in SEQ ID No. 5 are Ala and Asp, respectively, the amino acids in position 450 and 451 in SEQ ID No. 6 are Asp and Ala, respectively, the amino acids in position 449, 450 and 451 in SEQ ID No. 7 are Ala, Asp and Ala, respectively, the amino acid in position 521 in SEQ ID No. 8 is Ala and wherein the DNA pol I or the enzymatically active fragment thereof further lacks strand-displacement activity.

According to yet another aspect, said DNA pol I or an enzymatically fragment thereof comprises an amino acid sequence selected from the group consisting of SEQ ID No. 3, SEQ ID No. 4, SEQ ID No. 5, SEQ ID No. 6, SEQ ID No. 7 and SEQ ID No. 8.

According to some embodiments of the above aspects, the DNA pol I is a large fragment DNA pol I or an enzymatically fragment thereof lacking the 5'-3' exonuclease domain.

The present invention furthermore according to yet an aspect, provides a kit comprising:

(a) a first container comprising a DNA pol II derived 3'-5' exonuclease or an enzymatically active fragment thereof, wherein said DNA exonuclease is substantially without polymerase activity and wherein said exonuclease activity is irreversibly inactivated at temperatures above about 25° C.; and (b) a second container comprising DNA pol I such as a large fragment DNA polymerase or an enzymatically active fragment thereof, wherein said DNA polymerase is substantially without strand-displacement activity and wherein said DNA pol I is irreversibly inactivated at temperatures above about 25° C.

According to one aspect, the DNA pol II derived 3'-5' exonuclease in the first container and the DNA pol I in the second container is irreversible inactivated at temperatures above about 30° C.

According to yet another aspect, a kit is provided wherein the DNA pol II derived 3'-5' exonuclease or an enzymatically active fragment thereof of the first container exhibits 3'-5' exonuclease activity in the presence of dNTPs and the DNA pol I or an enzymatically active fragment thereof of the second container has 3'-5' exonuclease activity.

According to yet another aspect, a kit is provided wherein the DNA pol I of the second container is a large fragment DNA pol I.

According to yet another aspect, a kit is provided wherein the DNA pol II derived 3'-5' exonuclease or an enzymatically active fragment thereof of the first container comprises an amino acid sequences selected from the group consisting of SEQ ID No. 12, SEQ ID No. 13, SEQ ID No. 14, SEQ ID No. 15, SEQ ID No. 16 and SEQ ID No. 17 and wherein the DNA pol I or an enzymatically fragment thereof of the second container comprises an amino acid sequence selected from the group consisting of SEQ ID No. 3, SEQ ID No. 4, SEQ ID No. 5, SEQ ID No. 6 and SEQ ID No. 7.

According to a final aspect, a kit is provided for use in the process of the present invention.

FIGURES

FIG. 1 DNA assembly platform overview. Step A: Linearized vector and the DNA fragments containing Part X and Part Y are treated in the same vessel or in separately vessels with mutated DNA pol II (MV pol II) of the present invention.

Step B: The DNA pol II mutants of the present invention are shown in FIGS. 11A and B. The uniquely developed DNA pol II derived 3'-5' exonuclease will bind dsDNA and the 3'-5' exonuclease activity of the enzyme will chew-back the linearized vector and the DNA fragments from 3' to 5' (each homology region having complementary sequence identity is coded A, B and C). The exonuclease can operate in the presence of dNTPs. Since the enzyme is heat-labile the 3' to 5' exonuclease activity is inactivated during the reaction. Since the assembly reaction is performed at room temperature, the complementary single-stranded 5' overhangs only need to be around 10-40 bases long, also lowering the mutation chance occurring in the primer. Step C: The chewed-back linearized vector and DNA fragments are subsequently mixed and annealed in one reaction step. Step D: The developed proofreading DNA pol I (MG pol I) of the present invention is strand-displacement negative (SD−) and 5'-3'-exonuclease negative and is added to fill in possible gaps left behind between the annealed overhangs. The DNA pol I is also heat-labile, enabling multiple assemblies without pretreatment of each individual assembly reaction. The end result is a plasmid with nicks. Step E: Once transformed into competent *Escherichia coli* or other microbial cells, the nicks are repaired by a ligase of the host cell.

FIG. 2 shows the pGFPuv Vector from Clontech Laboratories, Inc., which is used for testing the enzyme variants generated. By choice of the primer pairs the desired number of fragments is produced by PCR and subsequently used as substrate in the DNA assembly technology illustrated in FIG. 1. The technology has been tested with two, three and four fragments.

FIG. 3 shows successful DNA assembly that is visible after transformation of the assembled plasmid into *E. coli* and thus green-fluorescent colonies due to the green-fluorescent protein that is encoded by the plasmid. DNA pol II enzyme used is the SM2 mutant (D568A). The mutants are illustrated in FIGS. 11A and B. The large fragment DNA pol I mutant used is the SDA (A450D/F451A-double mutant). The different mutants of the invention are illustrated in FIG. 7B.

Figures 7A, 7B:
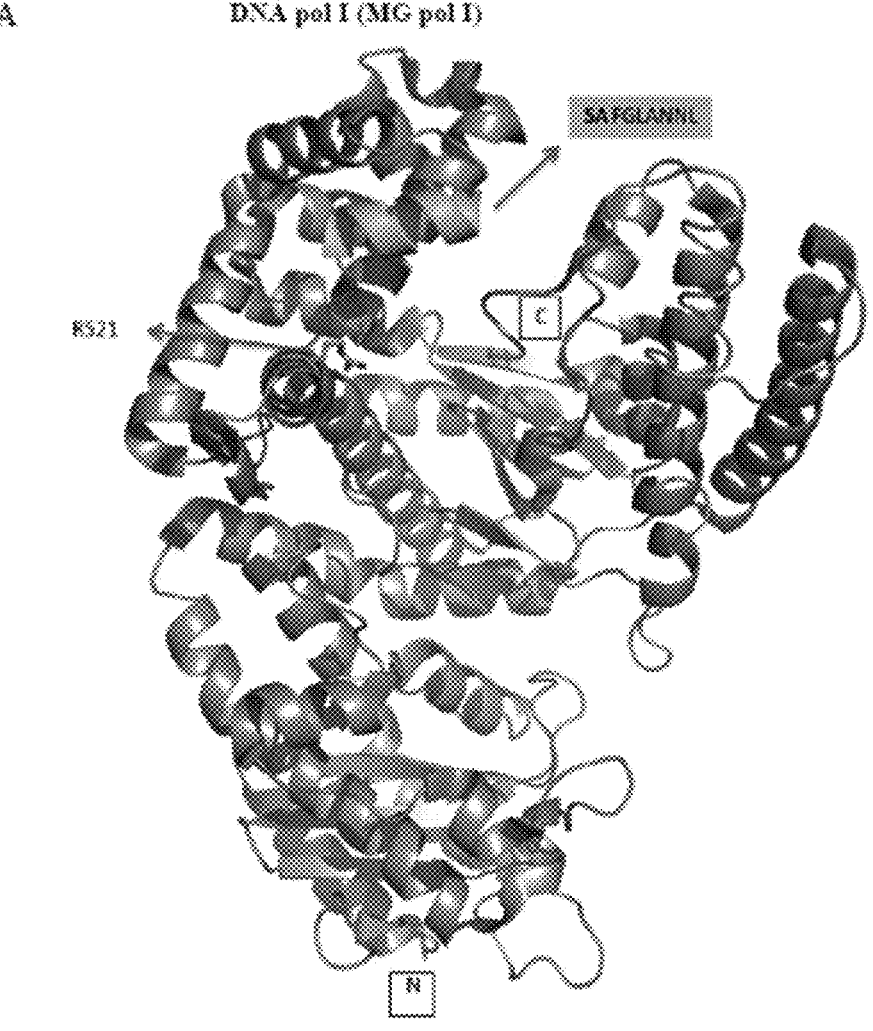

FIGS. 7A and B: (A) represents a model of the Klenow fragment (PDB code: 1D8Y), a homologous polymerase to the DNA polymerase I (MG pol I) of the present invention, illustrating the alpha helix identified by the arrow harboring the three consecutive amino acid residues 5449, A450 and F451, and also showing the position of residue R521, the C- and N-terminal end. (B) Amino-acid sequence in the wild type enzyme is Ser449-Ala450-Phe451 (SAF). The sequence numbering is according to the sequences having SEQ ID No. 1 and SEQ ID No. 2. The variants of DNA polymerase I contain a mutation at one, two or all three of these positions. The letters depict the amino-acid residue present at position 449, 450 and 451, respectively.

Figure 8:
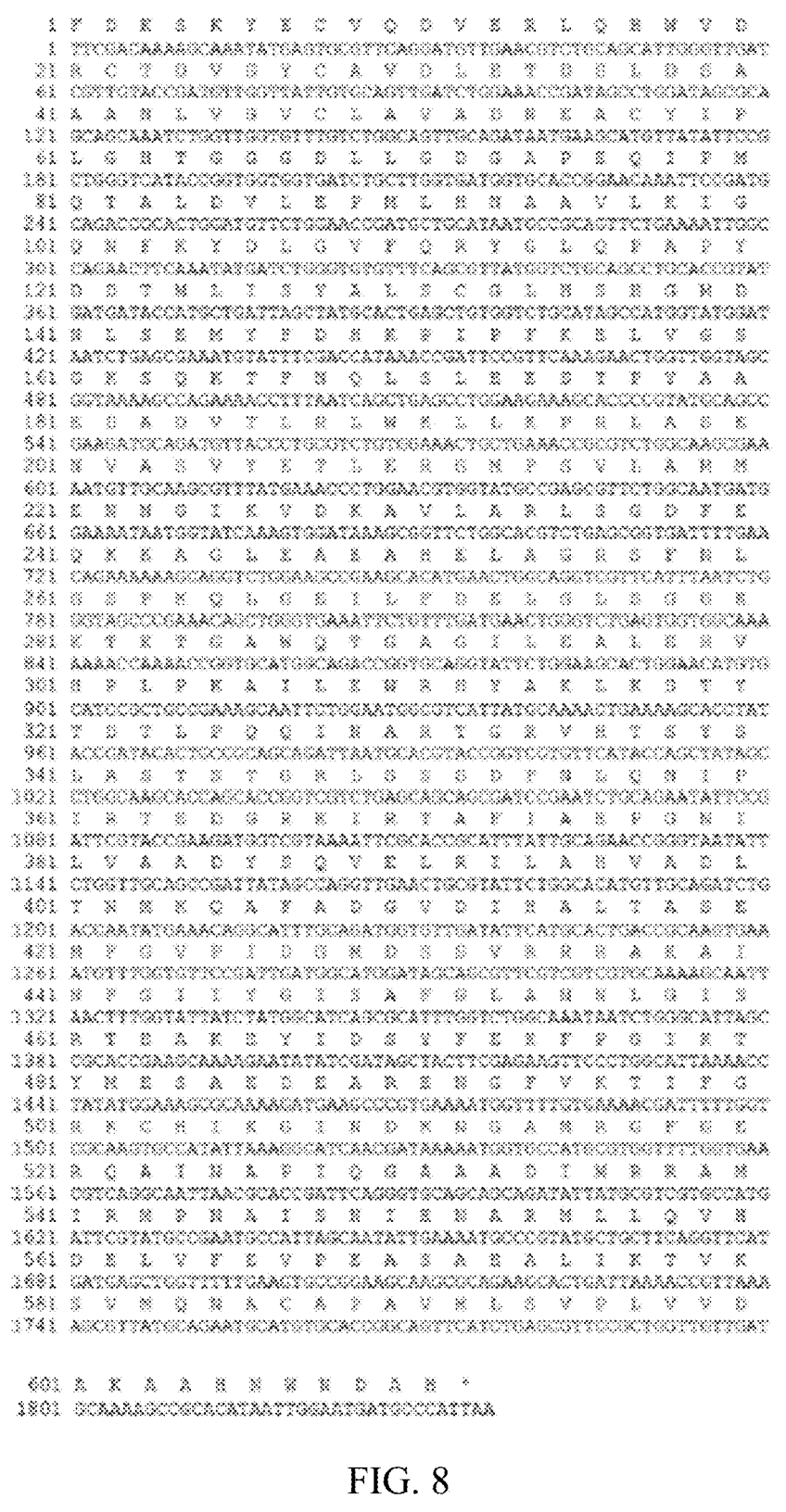

FIG. 8 shows the DNA and amino acid sequence of the large fragment DNA polymerase I (MG Pol I) of the present invention.

Figure 9:
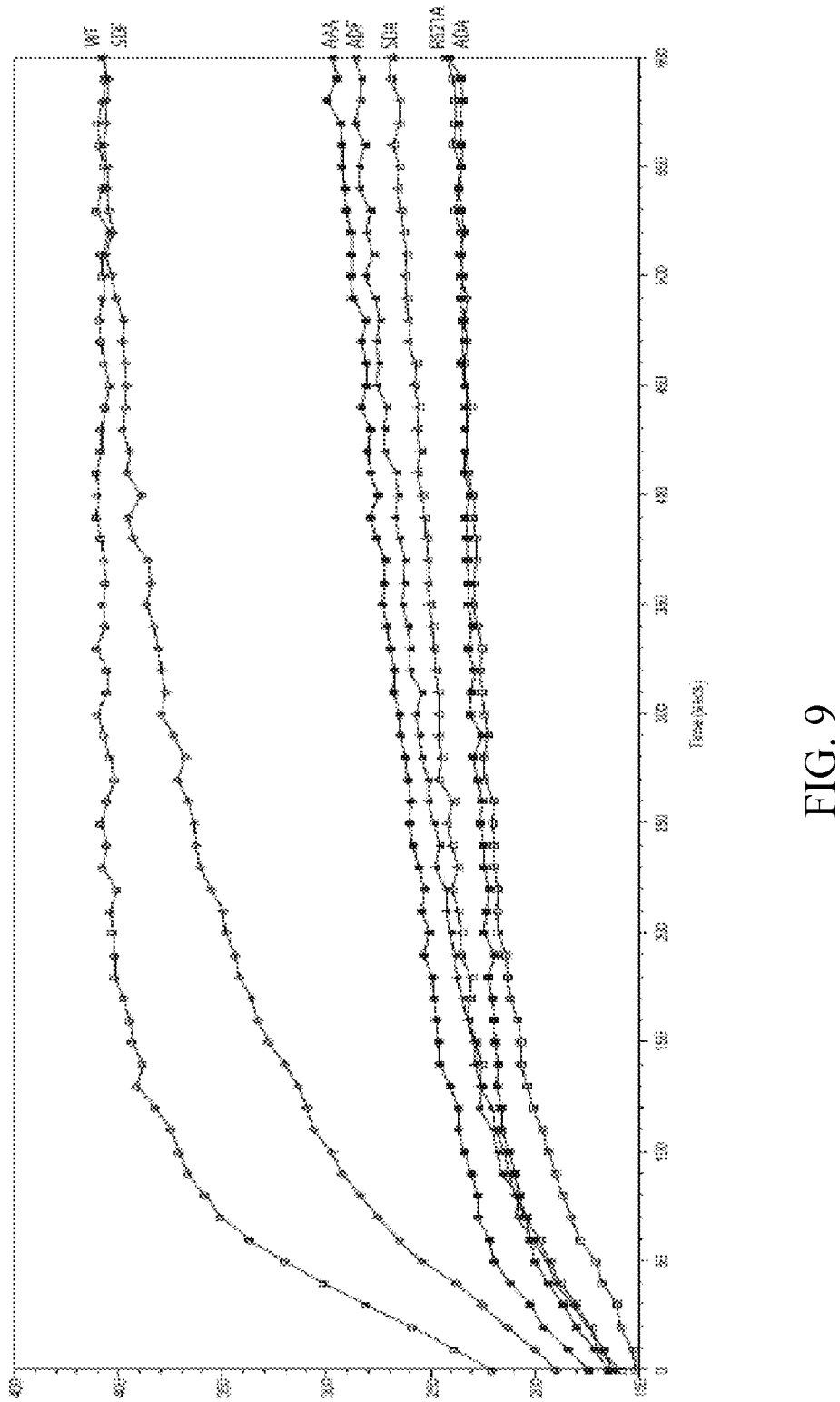

FIG. 9 shows a comparison of the polymerase activity of the large fragment DNA polymerases I (MG Pol I) of the present invention, represented by the wild type (wt) DNA polymerase, the A450D-mutant (SDF), S449A+F451A-mutant (AAA), S449A+A450D-mutant (ADF), the A450D+F451A-mutant (SDA), the S449A+A450D+F451A-mutant (ADA) and the R521A-mutant. RFU: relative fluorescence units.

Figure 10:
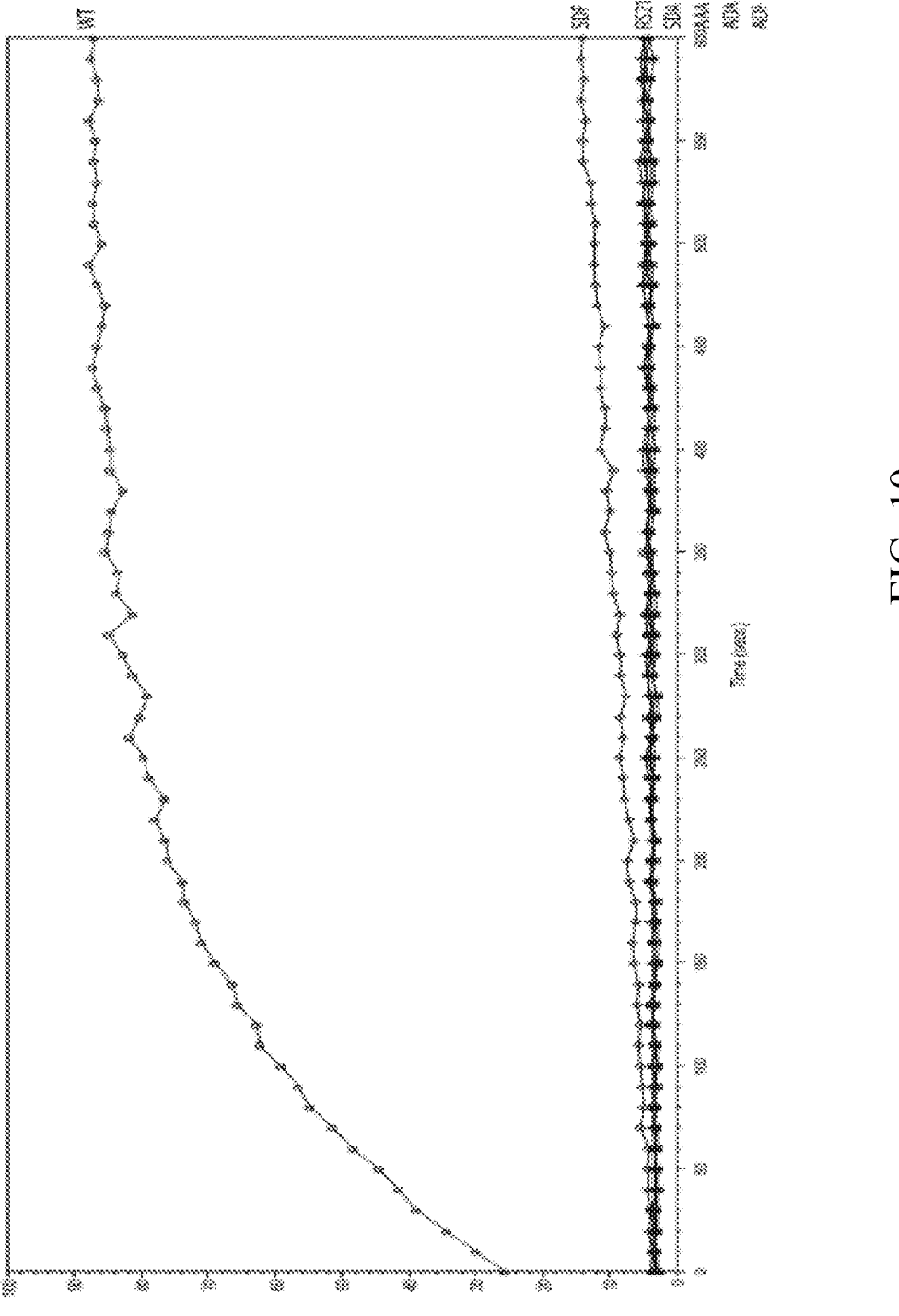

FIG. 10 shows a comparison of the strand displacement activity of the large fragment DNA polymerases I of the present invention, represented by the wild type (wt) DNA polymerase, the A450D-mutant (SDF), S449A+F451A-mutant (AAA), S449A+A450D-mutant (ADF), the A450D+F451A-mutant (SDA), the S449A+A450D+F451A-mutant (ADA) and the R521A-mutant. RFU: relative fluorescence units.

Figures 11A, 11B:
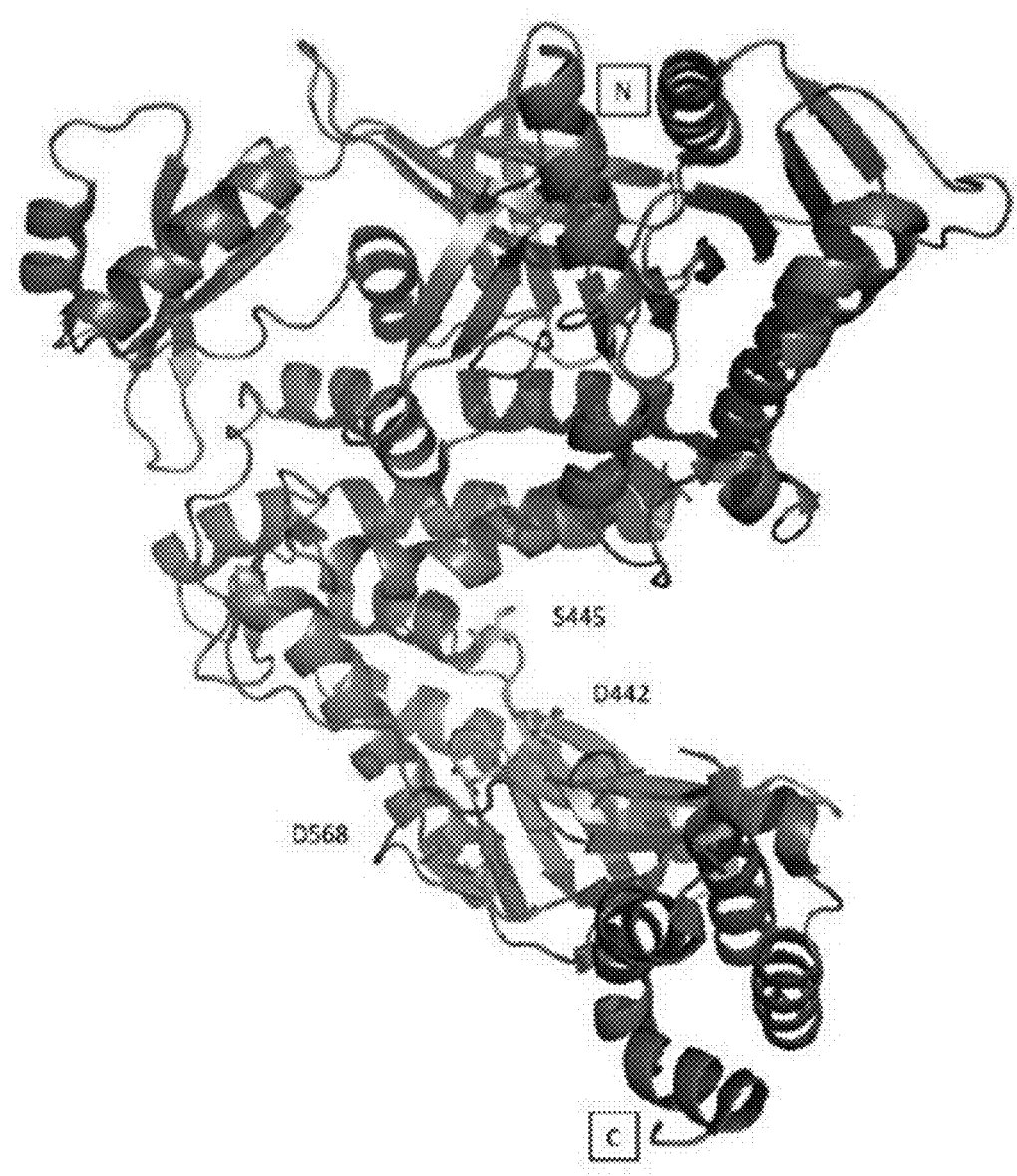

FIGS. 11A and B: (A) represents a model of DNA polymerase II from *E. coli* (PDB code: 1Q8I), a homologous protein to DNA polymerase II from *M. viscosa* (MV pol II) and illustrates the position of the amino acids D442, S445 and D568, as well as the C- and N-terminal end. (B) shows the different single and double DNA polymerases derived 3'-5' exonucleases (MV pol II) mutants according to the present invention.

Figure 12:
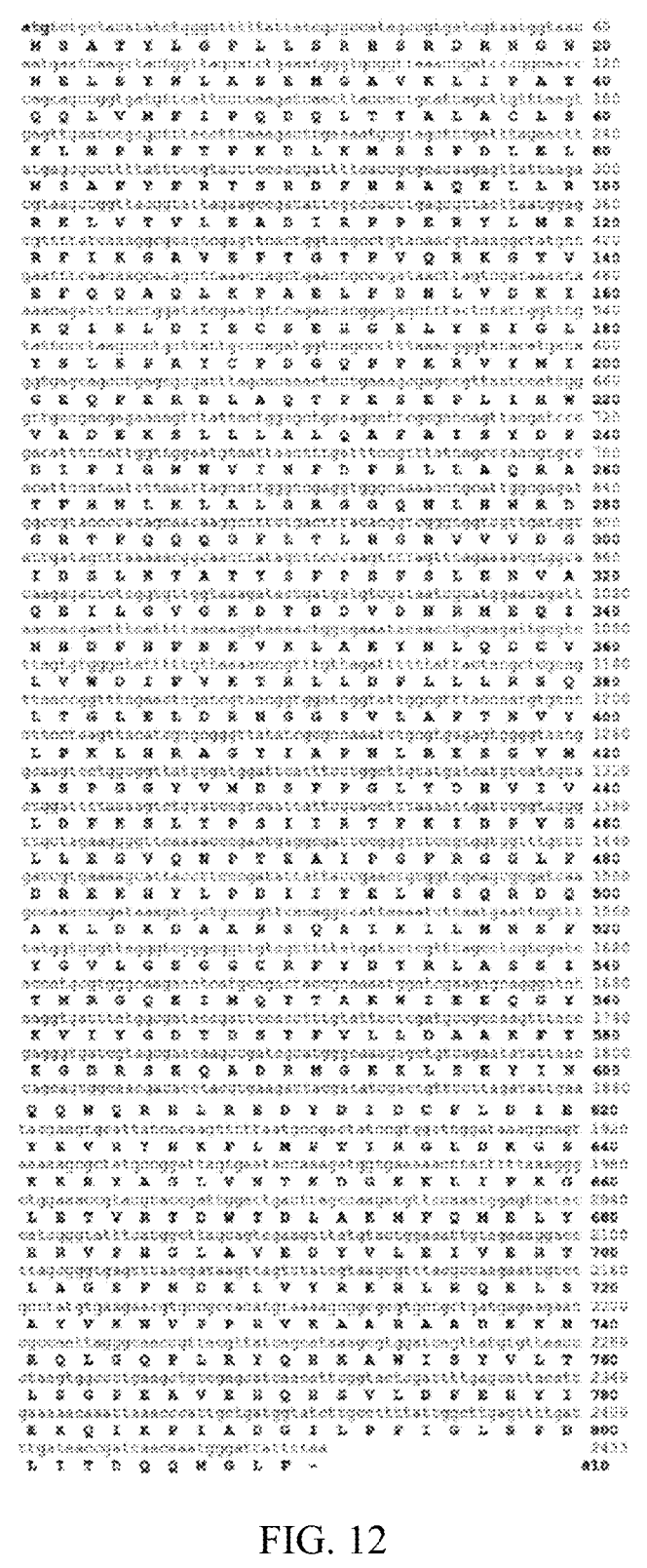

FIG. 12 shows the DNA and amino acid sequence of the DNA polymerases derived 3'-5' exonucleases (MV pol II) of the present invention.

Figure 13:
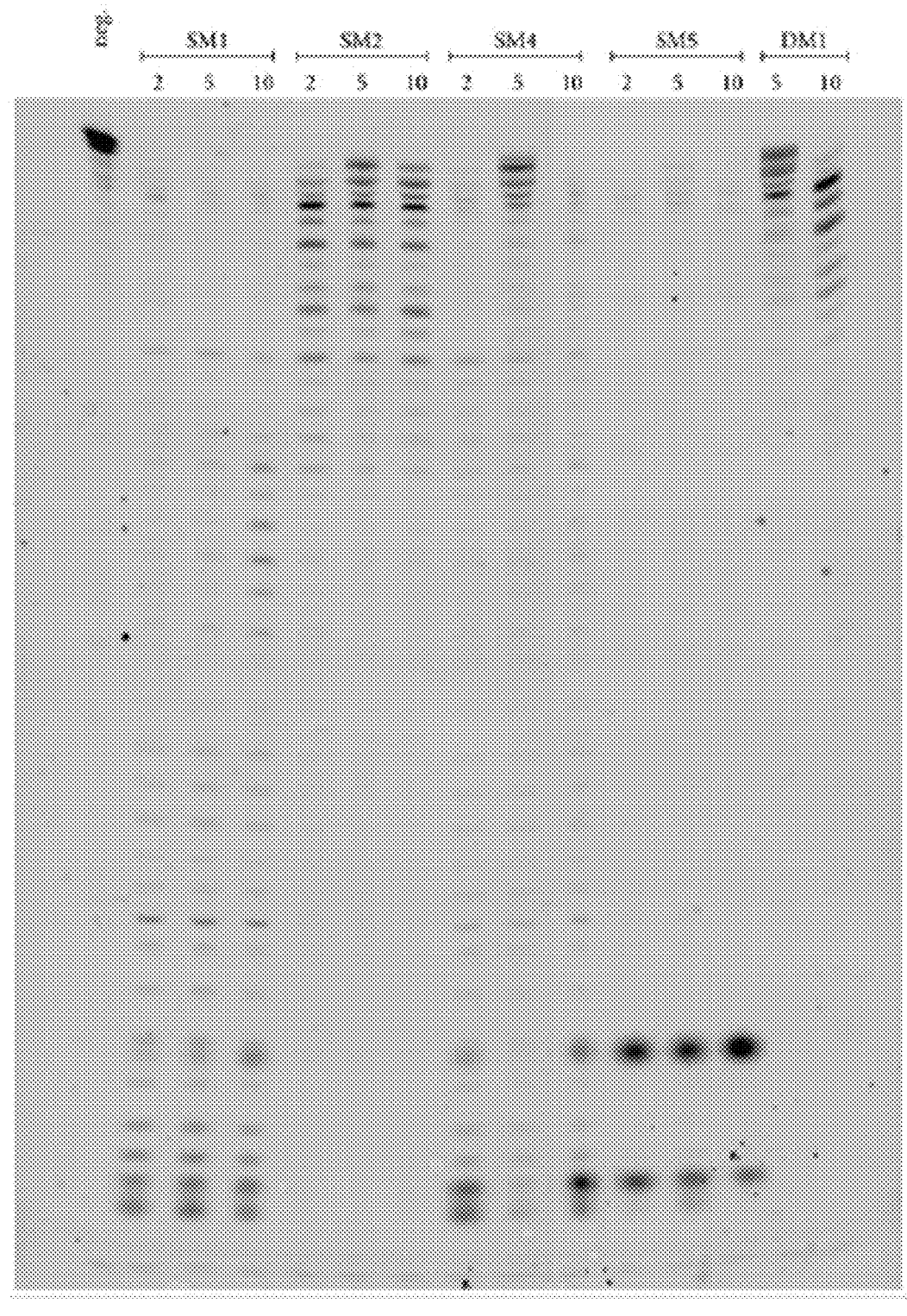

FIG. 13 shows exonuclease activity of DNA polymerases derived 3'-5' exonucleases (MV pol II) of the present invention.

DETAILED DESCRIPTION OF THE INVENTION

The present invention is as mentioned above based on the identification of two heat labile DNA polymerases of marine origin with advantageous characteristics and the providing of an improved multiple DNA assembly process. The present process inter alia allows for the assembly of a large number of dsDNA molecules at room temperature.

Unless specifically defined herein, all technical and scientific terms used have the same meaning as commonly understood by a skilled artisan in the fields of genetics, biochemistry, and molecular biology.

All methods and materials similar or equivalent to those described herein can be used in the practice or testing of the present invention, with suitable methods and materials being described herein. All publications, patent applications, patents and other references mentioned herein are incorporated by reference in their entirety. In case of conflict, the present specification, including definitions, will prevail.

Where a numeric limit or range is stated, the endpoints are included. Also, all values and sub ranges within a numerical limit or range are specifically included as if explicitly written out.

According to the present invention, the in vitro process for assembly of two or more dsDNA molecules are carried out at room temperature. The term "room temperature" is a recognized term in the art and includes temperatures in within the range of 18° C. to 25° C.

The first step of the in vitro process of the invention involves the providing of two or more linearized dsDNA molecules to be assembled, whereby the DNA molecules to be assembled share a region of sequence identity at their terminal regions such that the distal region of the one DNA molecule and the proximal region of the second DNA molecule share sequence identity. The region of sequence identity ensures that the at least two DNA molecules are combined in the desired order. The term "distal" as used herein refers to the 3' end of a first DNA molecule of a pair to be joined (the 5'-most DNA molecule), and the term "proximal" refers to the 5' end of the second DNA molecule of the pair.

The skilled person will acknowledge that the distal end of a first DNA molecule to be joined with a second DNA molecule will be complementary or sufficiently complementary to the proximal end of said second DNA molecule. If more than two DNA molecules are assembled, the distal end of the second DNA molecule will be complementary or sufficiently complementary to the proximal end of a third DNA molecule to be assembled, and so forth.

Thus, when a plurality of DNA molecules is to be assembled, for each pair of DNA molecules to be combined, the distal region of one of the DNA molecules of the pair is designed to share a region of sequence identity with the proximal region of the other DNA molecule of the pair. The distal and proximal regions of sequence identity for each pair of DNA molecules are designed to be unique (to be different from the regions of sequence identity of the other pairs of DNA molecules), ensuring that the order of the DNA molecules in the assembled DNA molecule can be predetermined.

The present process may be used to anneal at least two dsDNA molecules. In particular, the present process is useful for assembling a large number of dsDNA molecules.

The region of sequence identity should be sufficiently long to allow the assembly to occur. According to the present invention, the provided dsDNA molecules are contacted with a thermolabile (heat labile) 3'-5' exonuclease of marine origin (MV pol II). Upon contacting the DNA molecules to be assembled with the 3'-5' exonuclease according to the present invention, the digestion process will expose the single stranded sequences in the regions of sequence identity of the pairs of DNA molecules to be assembled. The overhang prepared in the distal end of one of the DNA molecules in a pair is complementary to or sufficiently complementary to the proximal end of the other pair of the DNA molecule.

The complementary or substantially complementary ends thus revealed are capable of being annealed. Complementary nucleotides are A and T (or A and U), or C and G. When referring to the term "substantially complementary", it is to be understood that two single stranded DNA molecules are substantially complementary when the nucleotides of one strand, optimally aligned and compared and with appropriate nucleotide insertions or deletions, pair with at least about 80% of the nucleotides of the other strand, and preferably 90%, 95%, or 100%. Furthermore, it is to be understood that "completely complementary sequences" or "exactly complementary sequences" have no mismatches at all, i.e., all G's of one strand are aligned with C's on the other strand and all A's with Ts on the other.

The length of the 5' overhang prepared in the exonuclease treatment step of the process of the invention can vary, such as comprising at least above 8 nucleotides (bases). According to one embodiment, 5' overhang is prepared being at least 10 nucleotides. According to another embodiment, the 5' overhang prepared in the exonuclease treatment step of the process of the invention is of a length within the range of 10-40 nucleotides. In the present process, a DNA molecule having a single stranded 5' overhangs of 10-40 nucleotides in the distal end will be sufficient to anneal to a DNA molecule having a complementary overhang of 10-40 nucleotides in the proximal end.

The time used for digestion the dsDNA molecules in question with the 3'-5' exonuclease may vary dependent upon the dsDNA molecules and the desired length of the 5'-overhang. For example, the 3'-5' exonuclease may be brought in contact with the two or more DNA molecules of step (b) of the present method for 5 minutes or more, such as 10 minutes or more, such as at 15 minutes or more, such as 20 minutes or more.

According to one embodiment, the 3'-5' exonuclease is brought in contact with the dsDNA molecules within a range of 5-30 minutes, such as within a range of 8-25 minutes, such as e.g. about 10-20 minutes, such as about 15 minutes.

The 3'-5' exonuclease digested dsDNA molecules to be combined are annealed through hybridization of overlaps under appropriate conditions. The skilled person will be well aware of conditions suitable for allowing to single stranded DNA sequences to hybridize. The skilled person will be aware of that the time needed for sufficient annealing to take place may vary dependent upon the conditions used, as well as the degree of complementarity of the overhangs of the pair of DNA molecules to be combined. According to one embodiment, the annealing step (c) of the present invention may be carried out for at least 5 minutes, such as for at least 10 minutes, such as for about 15 minutes, such as at least 20 minutes or more. The annealing step (c) may according to one embodiment be carried out within a range of 5-25 minutes, such as within a range of 8-20 minutes, such as e.g. about 10-15 minutes.

The two or more dsDNA molecules may be digested with the 3'-5' exonuclease in the same vessel or separately.

The 3'-5' exonuclease used in step (b) of the present process is as mentioned an exonuclease derived from a DNA polymerase II of marine origin. When used in the present process, said DNA polymerase II have been modified in order to inactivate, impair or reduce the polymerase activity. The 3'-5' exonuclease used in step (b) is therefore substantially without strand polymerase activity.

The expression "substantially without polymerase activity" is to be understood to mean that the active site of the polymerase activity of the enzyme of the invention is impaired or absent compared with the wild type DNA polymerase, said wild type DNA polymerase having an amino acid sequence according to SEQ ID No. 11. For example, the skilled person will acknowledge that a DNA polymerase having a polymerase activity that are reduced similar with the polymerase activity of a DNA polymerase derived 3-5' exonucleases having an amino acid sequence of SEQ ID NO. 1117 has an impaired polymerase activity, i.e. that are substantially without polymerase activity. The skilled person will furthermore acknowledge that polymerase activity can be measured using a real time molecular beacon assay, such as disclosed in Summerer, Methods Mol. Biol., 2008, 429, 225-235 or in modified form as shown in example 4 below.

Figure 4:
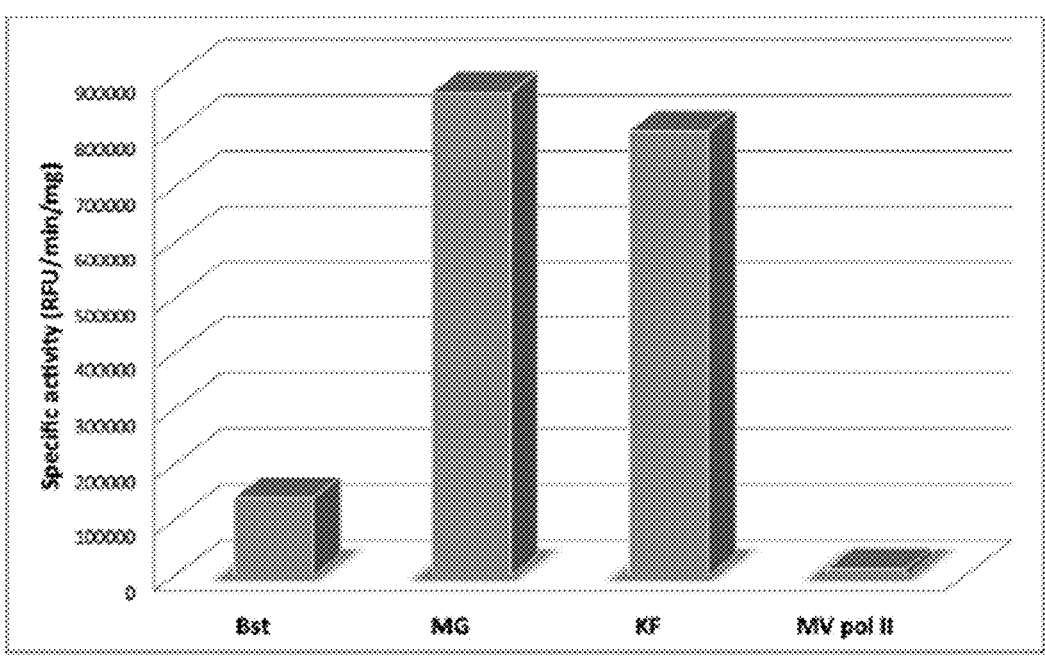
FIG. 4 shows the polymerase activity of the present large fragment DNA polymerase I (MG) and DNA polymerase II (MV pol II) compared with the polymerase activity of the Klenow enzyme from *E. coli* (KF) and the thermophilic *Bacillus stearothermophilus* polymerase (Bst).

As shown in FIG. 4, the DNA polymerase derived 3'-5' exonuclease of marine origin (MV Pol II) exerts only poor polymerase activity. According to one embodiment, the 3'-5' exonuclease used in step (b) of the present invention have sufficiently reduced polymerase activity. The term "sufficiently reduced polymerase activity", referring to 3'-5' exonuclease used in the present process, is to be understood to mean that the polymerase activity of the exonuclease used in step (b) has a polymerase activity that is equal to, similar or reduced compared with the polymerase activity of an enzyme having an amino acid selected from the group consisting of SEQ ID No1. 11, SEQ ID No. 12, SEQ ID No. 13, SEQ ID No. 14, SEQ ID No. 15, SEQ ID No. 16 and SEQ ID No. 17. According to one embodiment, the exonuclease used according to the present process has sufficiently reduced polymerase activity. According to another embodiment, the exonuclease used in the present process lacks DNA polymerase activity. No polymerase activity was detected upon testing of the provided mutants (SEQ ID No. 12, 13, 14, 15, 16 and 17) using the polymerase activity assay described herein, even in the presence of dNTPs.

After allowing the DNA sequences in question to anneal, the annealed sequences are subjected to a thermolabile (heat labile) DNA polymerase I (MG Pol I) of marine origin, wherein said DNA polymerase is substantially without strand displacement activity. The step whereby the annealed DNA molecules are brought in contact with said DNA polymerase I is carried out under conditions whereby the remining single-stranded gaps in the annealed fragments are filled in by the MG pol I enzyme thereby assembling the two or more dsDNA molecules.

The skilled person will be aware of that the time needed for DNA polymerase I of marine origin to fill in the gaps may vary dependent upon the conditions used, as well as the degree of complementarity of the overhangs of the pair of DNA molecules to be combined. According to one embodiment, step (d) of the present invention is be carried out for about 5 minutes or more, such as for about 10 minutes or more, such as for about 15 minutes or more, such as for about 20 minutes or more. Step (d) may according to one embodiment be carried out within a range of 5-30 minutes, such as within a range of 8-20 minutes, such as e.g. about 10-15 minutes.

The skilled person will acknowledge that conditions used in the exonuclease step and DNA polymerase step of the present invention may vary depending on the enzyme of choice. The 3'-5' exonuclease and the DNA polymerase I of marine origin used in the present process retain their advantageous activities within the conditions commonly used in molecular cloning processes, such as multiple DNA assembly processes well known to the skilled person, e.g. in respect of type and concentration of salt(s), pH conditions, etc. For example, well known buffers such as Tris buffer may be used having a pH within about 8.0 and about 8.5. The skilled person will acknowledge that the conditions used in the exonuclease step and DNA polymerase step may vary, e.g. that the salt concentration must be altered.

According to one aspect of the present process, step (b) may be performed at a pH of at least about 8.5 and in the presence of 25 mM or less NaCl and KCl, respectively.

According to another aspect of the present process, step (d) is performed at a pH of about 8 in the presence of NaCl and KCl, and wherein the amount of said salt is higher than in step (b). For example, NaCl and KCl may be present in a concentration of about 100 mM.

The process of the present invention may be performed at isothermal conditions, preferably at any temperature within the range of about 18° C. to about 25° C. According to one embodiment, the process is carried out at about 25° C.

The 3'-5' exonuclease of step (b) and the DNA polymerase of step (d) may be irreversible inactivated at a temperature above 30° C. Said enzymes will also after a sufficient time be irreversible inactivated at temperatures above 25° C.

The 3'-5' exonuclease and DNA polymerase I used in the process of the invention is both of marine origin. The 3'-5' exonuclease is a DNA polymerase II derived 3'-5' exonuclease identified in *Moritella viscosa* isolated from Atlantic salmon affected by winter ulcer disease. The DNA polymerase I was isolated by metagenomic analysis of samples collected in the artic area around Svalbard.

The identified 3'-5' exonuclease applicable in the present method may be a 3'-5' exonuclease or an enzymatically active fragment thereof comprising an amino acid selected from the group consisting of SEQ ID No. 12, SEQ ID No. 13, SEQ ID No. 14, SEQ ID No. 15, SEQ ID No. 16 and SEQ ID No. 17.

The 3'-5' exonuclease is a DNA polymerase II derived 3'-5' exonuclease enzyme or an enzymatically active fragment thereof wherein the enzyme or the enzymatically active fragment thereof comprising an amino acid sequences having at least about 60% sequence identity over the entire length of the sequence such as at least, 70%, 75%, 80%, 85%, 90%, 95%, 96%, 97%, 98%, or 99% sequence identity over the entire length of the sequence of any one of the sequences selected from the group consisting of SEQ ID No. 12, SEQ ID No. 13, SEQ ID No. 14, SEQ ID No. 15, SEQ ID No. 16 and SEQ ID No. 17 providing that the amino acid in position 442 in SEQ ID No. 12 is Ala;
the amino acid in position 568 in SEQ ID No. 13 is Ala;
the amino acid in position 442 in SEQ ID No. 14 is Glu;
the amino acid in position 568 in SEQ ID No. 15 is Glu;

the amino acid in position 442 and 568 in SEQ ID No. 16 is Ala; and the amino acid in position 445 in SEQ ID No. 17 is Arg and wherein DNA polymerase II derived 3'-5' exonuclease enzyme or the enzymatically active fragment thereof further lacks DNA polymerase activity.

The DNA pol I applicable in the present method may be a DNA polymerase such as a large fragment DNA polymerase or an enzymatically active fragment thereof comprising an amino acid sequences selected from the group consisting of SEQ ID No. 3, SEQ ID No. 4, SEQ ID No. 5, SEQ ID No. 6, SEQ ID No. 7 and SEQ ID No. 8.

The DNA pol I such as a large fragment DNA polymerase or an enzymatically active fragment thereof used in the present invention comprises an amino acid sequence having at least about 60% sequence identity over the entire length of the sequence such as at least, 70%, 75%, 80%, 85%, 90%, 95%, 96%, 97%, 98%, or 99% sequence identity over the entire length of the sequence of any one of the sequences selected from the group consisting of SEQ ID No. 3, SEQ ID No. 4, SEQ ID No. 5, SEQ ID No. 6, SEQ ID No. 7 and SEQ ID No. 8 providing that the amino acid in position 450 in SEQ ID No. 3 is Asp, the amino acids in position 449 and 451 in SEQ ID No. 4 are Ala, the amino acids in position 449 and 450 in SEQ ID No. 5 are Ala and Asp, respectively, the amino acids in position 450 and 451 in SEQ ID No. 6 are Asp and Ala, respectively, the amino acids in position 449, 450 and 451 in SEQ ID No. 7 are Ala, Asp and Ala, respectively, the amino acid in position 521 in SEQ ID No. 8 is Ala and wherein the DNA pol I or the enzymatically active fragment thereof are substantially without strand displacement activity.

The expression "substantially without strand displacement activity" is to be understood to mean that the displacement activity of the DNA polymerase is impaired or absent compared with the wild type DNA polymerase having an amino acid sequence according to SEQ ID No. 2. For example, the skilled person will acknowledge that a DNA polymerase having a displacement activity that is reduced to the degree of the DNA polymerases having an amino acid sequence of SEQ ID NO. 3-8 has an impaired or inactivated strand displacement activity, i.e. that are substantially without strand displacement activity.

SEQ ID No. 1 and SEQ ID No. 2 are examples of large fragment DNA polymerase I sequences lacking the N-terminal 5'-3'-exonuclease domain.

The skilled person will understand that Large Fragment DNA Polymerase I, is a DNA polymerase enzyme that lacks the 5' to 3' exonuclease activity of intact DNA Polymerase I, but does exhibit the 5' to 3' DNA polymerase and 3' to 5' exonuclease activities. An example of a well-known large fragment DNA polymerase I is the Klenow fragment.

The expression "an enzymatically active fragment" of the above-mentioned enzymes is to be understood to mean an enzyme where the activity of the enzyme is maintained. For example, an enzymatically active fragment of the DNA polymerase I used in step (d) of the present process is to be understood to have the same or at least similar polymerase activity as a DNA polymerase comprising an amino acid sequence selected from the group consisting of SEQ ID No. 3, SEQ ID No. 4, SEQ ID No. 5, SEQ ID No. 6, SEQ ID No. 7 and SEQ ID No. 8. Furthermore, an enzymatically active fragment of the 3'-5' exonuclease used in step (b) of the present process is to be understood to have the same or at least similar exonuclease activity as an exonuclease having an amino acid sequence selected from the group consisting of SEQ ID No. 11, SEQ ID No. 12, SEQ ID No. 13, SEQ ID No. 14, SEQ ID No. 15, SEQ ID No. 16 and SEQ ID No. 17.

The skilled person will acknowledge that one or more amino acid may be removed, e.g. in the C- or N-terminal end of an amino acid sequence, without affecting the activity of the protein.

The skilled person will acknowledge that amino acids are grouped dependent upon the chemical characteristics of the side chain. Amino acids are commonly classified as hydrophobic or hydrophilic and/or as having polar or non-polar side chain. Substitutions of one amino acid for another having the same biochemical characteristics are commonly known as conservative substitution. The skilled person will acknowledge that conservative substitutions can be introduced into an amino acid sequence of a protein, e.g. to the enzyme according to the present invention without altering the activity of said enzyme. Such modifications will thus be expected to constitute a biologically equivalent product. For example, conservative substitution of amino acids include substitution made among amino acids within the following groups:

Val, Ile, Leu, Met (amino acids with hydrophobic side chain)

Phe, Tyr, Trp (amino acids with hydrophobic side chain)

Arg, His, Lys (amino acids with positively charged side chain)

Ala, Gly (amino acids with small side chain)

Ser, Thr (amino acids with uncharged side chains)

Asn, Gln (amino acids with uncharged side chains)

Asp, Glu (amino acids with negative charged side chain)

Generally, a conservative amino acid substitution refers to an amino acid substitution that does not alter the relative charge or size characteristics of the protein in which the amino acid substitution is made, and thus seldom alter the three-dimensional structure of the protein, which is why the biological activity are neither altered significantly.

Also, the skilled person will understand that one or more amino acids may be deleted, inserted or added without altering the activity of the enzyme of the present invention.

It is thus to be understood modifications as described above (substitutions, deletions, insertions and additions of amino acids) may be introduced without essentially altering the activity of an enzyme.

As used herein, both in respect of proteins and nucleic acid molecules or fragment thereof, when referring to "sequence identity", a sequence having at least x % identity to a second sequence means that x % represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically.

The skilled person will acknowledge that alignment for purposes of determining percent amino acid sequence identity can be achieved in various ways that are within the skill in the art, for instance, using publicly available computer software such as ClustalOmega (Sievers F, Higgins DG (2018) *Protein Sci* 27:135-145), Protein BLAST (from National Center for Biotechnology Information (NCBI), USA) or commercially available software such as Megalign (DNASTAR) software. Those skilled in the art can determine appropriate parameters for measuring alignment, including any algorithms needed to achieve maximal alignment over the full length of the sequences being compared. NCBI BLAST is another example of software used to determine amino acid sequence identity (MacWilliam et al., *Nucleic Acids Res.* 2013 July; 41 (Web Server issue): W597-W600).

Upon assembly of multiple dsDNA molecules, the dsDNA molecules of interest may be assembled into a linearized vector or a transporter construct suitable for cloning of multiple dsDNA fragment. Thus, according to one embodiment, dsDNA molecules to be assembled consist of a linearized vector or transporter construct and at least one linearized dsDNA fragment to be inserted into the vector or transporter construct. For example, Gateway Destination vectors such as pHMGWA may be used. Various other Gateway cloning vectors are available, such as e.g. the pDONR vectors provided by ThermoFisher Scientific. Also, larger transporter constructs such as cosmids may be used.

The present invention furthermore relates to a kit comprising the 3'-5' exonuclease of marine origin and a DNA polymerase I of marine origin as described above. The kit according to the present invention is provided for generating designed multi DNA assembled constructs.

In particular, a kit is provided comprising a first container comprising a DNA pol II derived 3'-5' exonuclease or an enzymatically active fragment thereof, wherein said DNA exonuclease is substantially without polymerase activity and wherein said exonuclease activity is irreversibly inactivated at temperatures above about 30° C., more preferably at temperatures above about 25° C.; and a second container comprising DNA pol I or an enzymatically active fragment thereof, wherein said DNA polymerase is substantially without strand displacement activity and wherein said DNA pol I is irreversibly inactivated at temperatures above about 30° C., more preferably at temperatures above about 25° C.

The 3'-5' exonuclease comprised in the first container is according to one aspect a DNA polymerase II derived 3'-5' exonuclease enzyme or an enzymatically active fragment thereof comprising an amino acid sequence selected from the group consisting of SEQ ID No. 12, SEQ ID No. 13, SEQ ID No. 14, SEQ ID No. 15, SEQ ID No. 16 and SEQ ID No. 17 or having at least about 60% sequence identity over the entire length of the sequences selected from the group consisting of SEQ ID No. 12, SEQ ID No. 13, SEQ ID No. 14, SEQ ID No. 15, SEQ ID No. 16 and SEQ ID No. 17, respectively, and wherein the DNA polymerase II derived 3'-5' exonuclease enzyme or the enzymatically active fragment thereof further lacks DNA polymerase activity.

The DNA pol I comprised in the second container is according to one aspect a large fragment DNA polymerase or an enzymatically active fragment thereof comprising an amino acid sequence selected from the group consisting of SEQ ID No. 3, SEQ ID No. 4, SEQ ID No. 5, SEQ ID No. 6, SEQ ID NO. 7 and SEQ ID No. 8, or having at least about 60% sequence identity over the entire length of the sequence of any one of the sequences selected from the group consisting of SEQ ID No. 3, SEQ ID No. 4, SEQ ID No. 5, SEQ ID No. 6, SEQ ID No. 7 and SEQ ID No. 8, respectively, and wherein the large fragment DNA pol I or the enzymatically active fragment thereof further lacks strand-displacement activity A kit may also comprise a vector applicable in multiple DNA assembly processes.

The kit according to the present invention may furthermore comprise a third container comprising a vector or transporter construct such as a cosmid vector suitable for assembling multiple dsDNA fragments of interest.

EXAMPLES

Example 1: Identification of the DNA Polymerase I, Modification Thereof by Site-Directed Mutagenesis Upon analysis of a metagenome library originating from samples provided in Arctic area around Svalbard, a DNA sequence encoding a polymerase according to SEQ ID No. 2 were identified.

The vector pET151/D-TOPO® containing the codon-optimized gene encoding the large fragment of the identified DNA polymerase I (SEQ ID No. 9) was purchased from the Invitrogen GeneArt Gene Synthesis service from Thermo Fisher Scientific.

In order to provide modified enzymes, wherein the strand displacement activity of the identified enzyme is reduced, impaired or inactivated compared with the wild type enzyme, various mutations were introduced in SEQ ID No. 9 using the QuikChange II Site-Directed Mutagenesis Kit (Agilent Technologies). The introduced modification was confirmed by sequencing analysis.

Example 2: Preparation of Recombinant DNA Pol I (MG) of the Invention

Recombinant protein production of MG polymerase I large fragment and its mutants was performed in Rosetta 2 (DE3) cells (Novagen®). The cells grew in Terrific Broth media/ampicillin (100 μg/ml) and gene expression was induced at 0D600 nm 1.0 by addition of 0.1 mM IPTG. Protein production was carried out at 15° C. overnight. For protein purification the pellet of a ½-1 cultivation was resuspended in 50 mM HEPES pH 7.5 (at 25° C.), 500 mM NaCl, 5% glycerol, 1 mM DTT, pH 7.5, 0.15 mg/ml lysozyme, 1 protease inhibitor tablet (Complete™, Mini, EDTA-free Protease Inhibitor Cocktail, Roche) and incubated on ice for 30 min. Cell disruption was performed by sonication with the VCX 750 from Sonics® (pulse 1.0/1.0, 15 min, amplitude 25%). In the first step, the soluble part of the His$_6$-tagged protein present after centrifugation (48384 g, 45 min, 4° C.) and filtration (Ø 0.45 μm) was purified by immobilized Ni$^{2+}$-affinity chromatography. After a wash step with 50 mM HEPES, 500 mM NaCl, 35 mM imidazole, 5% glycerol, 1 mM DTT, pH 7.5 the protein was eluted at an imidazole concentration of 250 mM and further transferred into 50 mM HEPES, 500 mM NaCl, 10 mM MgCl$_2$, 5% glycerol, pH 7.5 by use of a desalting column. The second step was the cleavage of the tag by the TEV protease performed over night at 4° C. in 50 mM Tris pH 8.0, 0.5 mM EDTA and 1 mM DTT. To separate the protein from the His$_6$-tag and the His$_6$-tagged TEV protease a second Ni$^{2+}$-affinity chromatography has been performed in the third step by applying 50 mM HEPES, 500 mM NaCl, 5% glycerol, 1 mM DTT, pH 7.5. The final protein solution was concentrated and stored with 50% glycerol at −20° C. for activity assays.

Example 3 Cloning of DNA Polymerase II Derived 3'-5' Exonuclease and Site-Directed Mutagenisis Lunder et al. reported in Disease of Aquatic Organisms, vol. 23, No. 23, pp. 39-49 in 1995 experiments with a *Vibrio* like bacterium isolated from farmed Atlantic salmon affected by winter ulcer disease. Later, it was found that the isolated bacterium was a psychotrophic marine *Moritella viscosa* bacterium.

The providing of the gene encoding the enzyme of the present enzyme was obtained using the below primers in polymerase chain reaction using genomic DNA of said *M. viscosa* (GenBank: LN554852.1).

The identified gene encoding DNA polymerase II from *Moritella viscosa* was cloned into the pHMGWA vector using the Gateway® Technology (Thermo Fisher). Starting material for the polymerase chain reaction was the genomic DNA of *Moritella viscosa*.

The various mutations were introduced using the QuikChange II Site-Directed Mutagenesis Kit (Agilent Technologies) and confirmed by sequencing analysis.

```
forward primer
                                    (SEQ ID No. 19)
5'-CACCTTGTCTGCTACATATCTGGGT-3' reverse primer
                                    (SEQ ID NO. 20)
5'-TTAAAATAATCCCATTTGTTGATCGGTTATCA-3'.
```

In order to provide modified enzymes, wherein the polymerase activity of the identified enzyme is reduced, impaired or inactivated compared with the wild type enzyme, various mutations were introduced in the identified cloned gene by QuikChange II Site-Directed Mutagenesis Kit (Agilent Technologies) and confirmed by sequencing analysis.

Example 4: Preparation of Recombinant Enzyme (MV Pol II and Mutants Thereof)

For expression of the DNA pol II enzymes of the present invention in host cells, gene sequences encoding the present DNA polymerase (SEQ ID No. 18, codon optimized for the host cells in question) was introduced in the Gateway Destination Vector pHMGWA.

Recombinant protein production of the enzyme according to the present invention was performed in Rosetta 2 (DE3) cells (Novagen®). The cells grew in Terrific Broth media/ampicillin (100 µg/ml) and gene expression was induced at $OD_{600}$ nm 1.0 by addition of 0.1 mM IPTG. Protein production was carried out at 15° C. for 6-8 h.

For protein purification the pellet of a 1-1 cultivation was resuspended in 50 mM HEPES pH 7.5 (at 25° C.), 500 mM NaCl, 5% glycerol, 0.15 mg/ml lysozyme, 1 protease inhibitor tablet (Complete™, Mini, EDTA-free Protease Inhibitor Cocktail, Roche) and incubated on ice for 30 min.

Cell disruption was performed by sonication with the VCX 750 from Sonics® (pulse 1.0/1.0, 15 min, amplitude 25%). In the first step, the soluble part of the $His_6$-tagged protein present after centrifugation (48384 g, 45 min, 4° C.) and filtration (Ø 0.45 µm) was purified by immobilized $Ni^{2+}$-affinity chromatography. After a wash step with 50 mM HEPES (at 25° C.), 500 mM NaCl, 35 mM imidazole, 5% glycerol, the protein was eluted at an imidazole concentration of 250 mM and further transferred into 50 mM HEPES (at 25° C.), 500 mM NaCl, 10 mM $MgCl_2$, 5% glycerol by use of a desalting column. The second step was the cleavage of the tag by the TEV protease performed over night at 4° C. in 50 mM Tris pH 8.0, 0.5 mM EDTA and 1 mM DTT. To separate the protein from the $His_6$-tag and the $His_6$-tagged TEV protease a second $Ni^{2+}$-affinity chromatography has been performed in the third step by applying 50 mM HEPES (at 25° C.), 500 mM NaCl, 5% glycerol. The final protein solution was concentrated and stored with 50% glycerol at –20° C. for activity assays.

Example 5: Measuring the Polymerase Activity of the Present DNA Pol I (MG Pol I) and DNA Pol II Enzyme (MV Pol II)

In order to measure the polymerase activity of the present enzyme and also compare said novel enzyme with known DNA polymerases, an assay based on a molecular beacon probe (modified from Summerer, *Methods Mol. Biol.*, 2008, 429, 225-235) was used. The molecular beacon template consists of a 23mer loop that is connected by a GC-rich 8mer stem region (sequence is indicated in italics) and a 43mer extension. Due to the loop formation the fluorophores Dabcyl and FAM are in close proximity and thus quenched. Upon extension by the DNA polymerase I of the primer that is annealed to the molecular beacon template the stem is opened and the increase in distance of the two fluorophores is measured by the restoration of FAM fluorescence (excitation 485 nm, emission 518 nm).

```
molecular beacon template
                                    (SEQ ID. No. 21)
5' GGCCCGT^{Dabcyl}AGGAGGAAAGGACATCTTCTAGCAT^{FAM}ACGGGCCGT
CA-AGTTCATGGCCAGTCAAGTCGTCAGAAATTTCGCACCAC-3' primer
                                    (SEQ ID. No. 22)
5'-GTGGTGCGAAATTTCTGAC-3'
```

The molecular beacon substrate was produced by incubating 20 µl of 10 µM molecular beacon template and 15 µM primer in 10 mM Tris-HCl pH 8.0, 100 mM NaCl for 5 min at 95° C. The reaction was then let to cool down at room temperature for 2 h. The substrate solution was stored at –20° C. with a final concentration of 10 µM.

Fifty microliter reactions consisted of 200 nM substrate and 200 µM dNTP (equimolar amounts of dATP, dGTP, dCTP and dTTP). The reaction further contained 5 mM $MgCl_2$ in 50 mM Tris-HCl pH 8.5, 100 mM KCl, 1 mM DTT, 0.2 mg/ml BSA and 2% glycerol. The activity assay was carried out at 25° C. in black 96-well fluorescence assay plates (Corning®). The reaction was initiated by addition of protein solution, i.e. MG pol I and its variants. The increase in FAM fluorescence was measured as relative fluorescence units in appropriate time intervals by exciting at 485 nm and emission at 518 nm. The measurement was performed in a SpectraMax® Gemini Microplate Reader (Molecular Devices).

The results are shown in FIG. 4 shows that the DNA pol II (MV pol II) enzyme of the present invention has a low DNA polymerase activity compared to other known enzymes while DNA pol I (MG) of the present invention has a higher polymerase activity compared to other known polymerases. FIG. 9 shows the large fragment DNA polymerase activity of the different DNA pol I mutants compared to the polymerase activity of the wild-type enzyme.

Example 6: Strand Displacement Activity Assay

The assay is based on an increase in fluorescence signal that is measured upon displacement of the quenched reporter strand. This is only achievable through strand-displacement activity of the DNA polymerase.

The substrate for the strand-displacement activity assay consists of a "cold" primer of 19 oligonucleotides and a reporter strand consisting of 20 oligonucleotides that is labeled with the TAMRA fluorophore [TAMRA] at its 3' end. The template strand consists of 40 oligonucleotides and is labeled with the Black Hole Quencher 2 (BHQ2) at its 5' end. The primers are annealed to the template strand leaving a one-nucleotide gap at position 20 on the template strand. Furthermore, are the labels in close proximity and thus the fluorophore TAMRA is quenched by BHQ2. Upon strand-displacement activity of the DNA polymerase I the TAMRA labeled oligonucleotide is displaced from the template strand. As a consequence, the fluorophore and the quencher are no longer in close proximity and an increase in TAMRA fluorescence can be measured (excitation 525 nm, emission 598 nm).

```
                                           (SEQ ID No. 25)
5'-TATCCACCAATACTACCCTCGATACTTTGTCCACTCAAT[TAMRA]-
3'

(SEQ ID No. 26)
3'-ATAGGTGGTTATGATGGGATGCTATGAAACAGGTGAGTTA[BHQ2]-
5'
```

The strand-displacement activity of the DNA polymerase of the present invention and its variants expressed as mRFU/min/µg has been analyzed using the above-described strand-displacement activity assay.

The substrate for the strand-displacement activity assay was produced by incubating 20 µl of 10 µM "cold" primer, 10 µM reporter strand and 10 µM template strand in 10 mM Tris-HCl pH 8.0, 100 mM NaCl at 95° C. for 5 min. The reaction was then let to cool down at room temperature for 2 h. The substrate solution was stored at −20° C. with a final concentration of 10 µM.

Fifty microliter reactions consisted of 200 nM substrate and 200 µM dNTP (equimolar amounts of dATP, dGTP, dCTP and dTTP). The reaction further contained 5 mM MgCl₂ in 50 mM Tris-HCl pH 8.5, 100 mM KCl, 1 mM DTT, 0.2 mg/ml BSA and 2% glycerol. The activity assay was carried out at 25° C. in black 96-well fluorescence assay plates (Corning®). The reaction was initiated by addition of protein solution, i.e. Mg pol I and its variants. The increase in TAMRA fluorescence was measured as relative fluorescence units in appropriate time intervals by exciting at 525 nm and recording emission at 598 nm. The measurement was performed in a SpectraMax® M2ᵉ Microplate Reader (Molecular Devices).

The results of the analysis are shown in FIG. 10 and show that the mutant enzymes generated all have a very low or insignificant strand-displacement activity.

Example 7: 3'-5' Exonuclease Activity of the Present DNA Pol II (MV) Enzyme

The blunt-ended dsDNA substrate for the exonuclease assay was produced by incubation of 40 µl 0.5 µM template DNA with 0.5 µM FAM-labeled reverse complementary strand (SEQ ID No, 14 and SEQ ID No. 15) in 10 mM Tris-HCl pH 8.0, 100 mM NaCl at 75° C. for 5 min. The reaction was then let to cool down at room temperature for 2 h. The substrate solution was stored at −20° C. with a final concentration of 0.5 µM.

Ten microliter reactions contained 25 nM substrate, 5 mM MgCl₂ in 50 mM Tris-HCl pH 8.0, 25 mM NaCl, 1 mM DTT, 0.2 mg/ml BSA and 2% glycerol. The reactions were initiated by addition of 0.02 µg/µl protein, i.e. MV pol II and its variants. As a negative control protein dilution buffer has been used instead of protein solution. Reactions were stopped by addition of 2.5 µl denaturing gel loading buffer (95% formamide, 10 mM EDTA, 0.1% xylene cyanol) and incubation at 95° C. for 5 minutes. For the denaturing polyacrylamide gel electrophoresis (12% polyacrylamide/7 M urea) a sample volume of 6 µl was loaded onto the gel. The gel electrophoresis was performed in 0.5×TBE buffer (44.5 mM Tris, 44.5 mM boric acid, 1 mM EDTA) at 50 W for 1 hour 15 minutes and the gel subsequently scanned with the PharosFX Plus Imager (Bio-Rad).

```
                                          (SEQ ID. No. 23)
5'-[FAM]TATCCACCAATACTACCCTACGATACTTTGTCCACTCAAT-
3'

(SEQ ID. No. 24)
3'-ATAGGTGGTTATGATGGGATGCTATGAAACAGGTGAGTTA-5'
```

Figure 5:
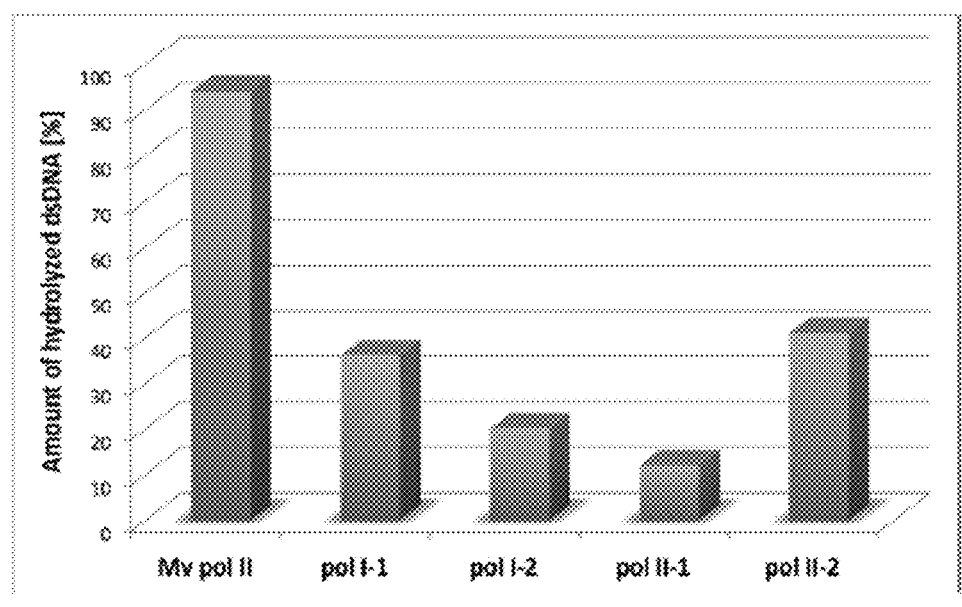
FIG. 5 shows the results from a comparison of the 3'-5' exonuclease activity of the MV pol II of the present invention (wild-type) and selected marine DNA polymerase (I and II) measured on $^3$H-dTTP radiolabeled linear blunt end dsDNA.
Figure 6:
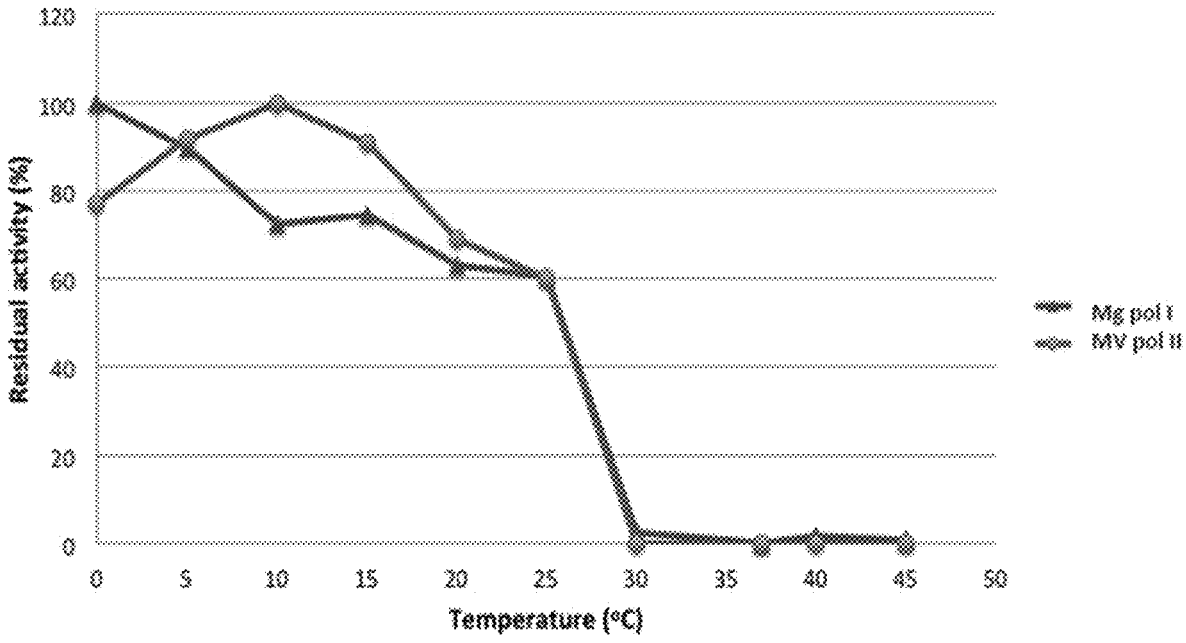
FIG. 6 shows the results of experiment measuring the residual enzymatic activity at 25° C. of the present wild type large fragment DNA polymerase I (MG) "triangle" and DNA polymerase II (MV) "circles" after incubation of each enzyme at various temperatures.

The results of the analysis are shown in FIG. 5 (comparison with other known marine enzymes) and 13 (comparison of different DNA pol II mutants of the present invention).

Figure 1:
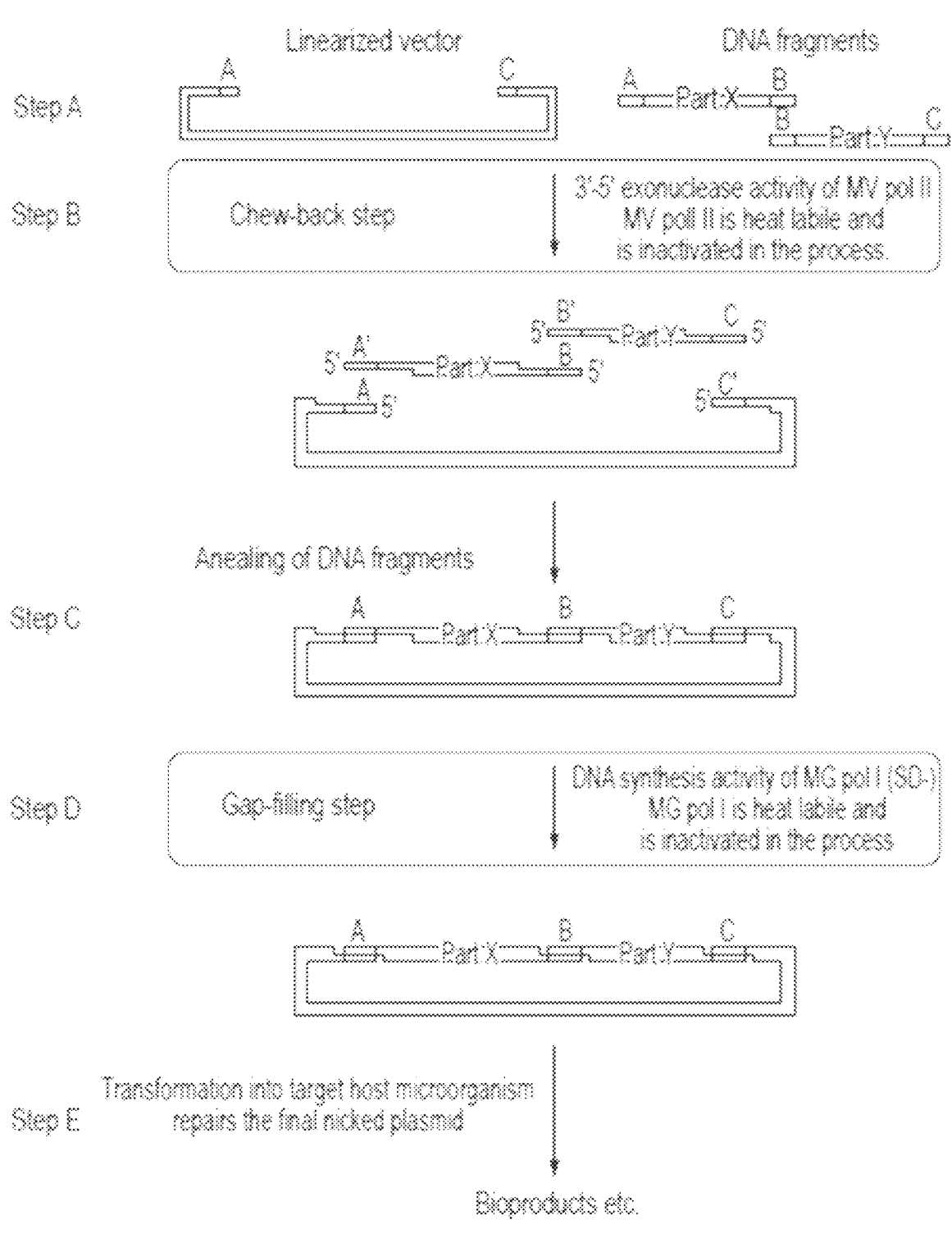

Example 8: DNA Assembly Platform Overview (See FIG. 1)

Step A: Linearized vector and the DNA fragments containing Part X and Part Y are treated in the same vessel or in separately vessels with mutated DNA pol II (MV pol II) of the present invention. Step B: The DNA pol II mutants of the present invention are shown in FIGS. 11A and B. The uniquely developed DNA pol II derived 3'-5' exonuclease will bind dsDNA and the 3'-5' exonuclease activity of the enzyme will chew-back the linearized vector and the DNA fragments from 3' to 5' (each homology region having complementary sequence identity is coded A, B and C). The exonuclease can operate in the presence of dNTPs. Since the enzyme is heat-labile the 3' to 5' exonuclease activity is inactivated during the reaction. Since the assembly reaction is performed at room temperature, the complementary single-stranded 5' overhangs only need to be around 10-40 bases long, also lowering the mutation chance occurring in the primer. Step C: The chewed-back linearized vector and DNA fragments are subsequently mixed and annealed in one reaction step. Step D: The developed proofreading large fragment DNA pol I (MG pol I) of the present invention is strand-displacement negative (SD−) and is added to fill in possible gaps left behind between the annealed overhangs. The large fragment DNA pol I is also heat-labile, enabling multiple assemblies without pretreatment of each individual assembly reaction. A suitable formulated master buffer is used for both enzymatic steps (the Chew-back step and the Gap-filling step) shown in the gray shaded boxes. The end result is a plasmid with single-stranded gaps or nicks. Step E: Once transformed into competent *Escherichia coli* or other microbial cells, the nicks are repaired by a ligase of the host cell.

Figure 2:
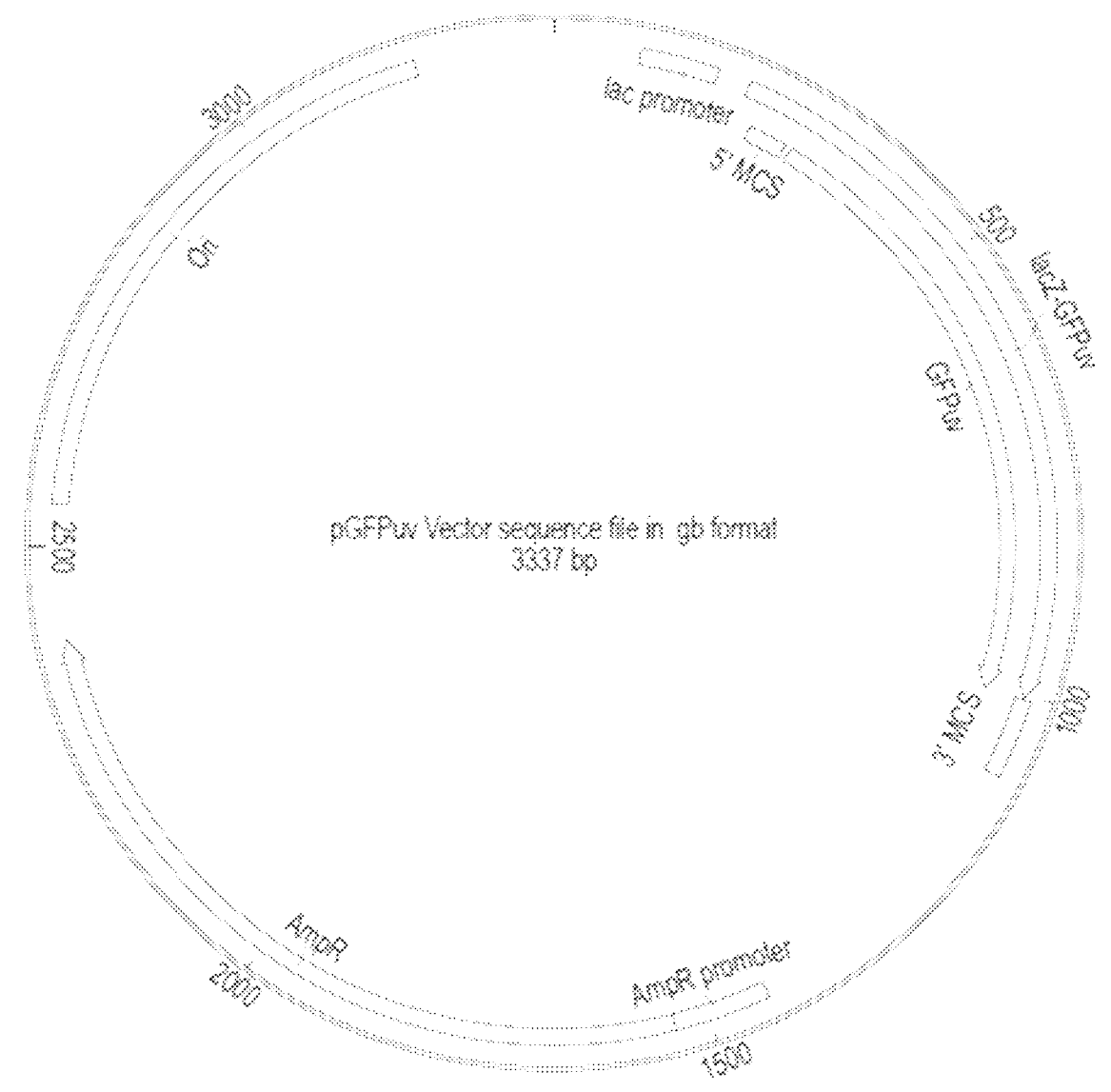
Figure 3:

The results of the assembly of three DNA fragments (1845 bp, 750 bp and 750 bp, respectively) is shown in FIG. 3 and the vector used for the experiment is shown in FIG. 2.

Overview of the Sequence Numbers Referred to in the Specification and Sequence Listing

| SEQ ID No. | Sequence information |
| --- | --- |
| 1 | Large fragment DNA polymerase I with variable amino acid positions 449, 450, 451 and 521 |

| SEQ ID No. | Sequence information |
|---|---|
| 2 | Wild type sequence of large fragment DNA polymerase I of marine origin identified by metagenomic analysis with optimized codons |
| 3 | DNA polymerase I wherein alanine in position 450 is replace by aspartate compared with the wild type sequence SEQ ID No. 2 (A450D SDF) |
| 4 | DNA polymerase I wherein serine in position 449 and phenylalanine in position 451 is replace by alanine compared with the wild type sequence SEQ ID No. 2 (S449A/F451A, AAA) |
| 5 | DNA polymerase I wherein serine in position 449 and alanine in 450 is replace by alanine and aspartate, respectively, compared with the wild type sequence SEQ ID No. 2 (S449A/A450D, ADF) |
| 6 | DNA polymerase I wherein alanine in position 450 and phenylalanine in position 450 is replaced by aspartate and alanine, respectively compared with the wild type sequence SEQ ID No. 2 (A450D/F451A, SDA) |
| 7 | DNA polymerase I wherein serine in position 449 and alanine in position 450 and aspartate in position 451 is replace by alanine, aspartate and alanine, respectively compared with the wild type sequence SEQ ID No. 2 (S449A/A450D/D451A, ADA) |
| 8 | DNA polymerase I wherein argininein position 521 is replaced by alanine compared with the wild type sequence SEQ ID No. 2 (R521A) |
| 9 | Nucleic acid sequence encoding a DNA polymerase I comprising an amino acid sequence according to SEQ ID No. 2 |
| 10 | DNA polymerase II derived 3'-5' exonuclease with variable amino acid positions 442, 445 and 568. |
| 11 | Wild type sequence of DNA polymerase II derived 3'-5' exonuclease identified in Moritella viscosa. |

| SEQ ID No. | Sequence information |
|---|---|
| 12 | DNA polymerase II derived 3'-5' exonuclease wherein aspartate in position 442 is replace by alanine compared with the wild type sequence SEQ ID No. 11 (D442A, SM1) |
| 13 | DNA polymerase II derived 3'-5' exonuclease wherein aspartate in position 568 is replaced by alanine compared with the wild type sequence SEQ ID No. 11 (D568A, SM2) |
| 14 | DNA polymerase II derived 3'-5' exonuclease wherein aspartate in position 442 is replaced by glutamate compared with the wild type sequence SEQ ID No. 11 (D442E, SM4) |
| 15 | DNA polymerase II derived 3'-5' exonuclease wherein aspartate in position 568 is replaced by glutamate compared with the wild type sequence SEQ ID No. 11 (D568E, SM5) |
| 16 | DNA polymerase II derived 3'-5' exonuclease wherein aspartate in position 442 and 568 is replaced by alanine, respectively compared with the wild type sequence SEQ ID No. 11 (D442A/D568A, DM1) |
| 17 | DNA polymerase II derived 3'-5' exonuclease wherein serine in position 445 is replaced by arginine compared with the wild type sequence SEQ ID No. 11 (S445R) |
| 18 | Nucleic acid sequence encoding a DNA polymerase II comprising an amino acid sequence according to SEQ ID No. 11 with optimized codons |
| 19 | forward primer used in cloning of wild type DNA polymerase II gene |
| 20 | reverse primer used in cloning of wild type DNA polymerase II gene |
| 21 | molecular beacon template used in polymerase activity experiment |
| 22 | primer used in polymerase activity experiment |
| 23 | 5'-3' sequence used in exonuclease activity experiment |
| 24 | 3'-5'sequence used in exonuclease activity experiment |
| 25 | Sequence used in strand displacement activity experiment |
| 26 | Sequence used in strand displacement activity experiment |

The invention claimed is:

1. An in vitro process for assembly of two or more double-stranded (ds) DNA molecules wherein the assembly process takes place at room temperature and wherein said process comprises the steps of:

(a) providing two or more linearized dsDNA molecules to be assembled, whereby the DNA molecules to be assembled share a region of sequence identity at their terminal regions such that the distal region of the one DNA molecule and the proximal region of the second DNA molecule share sequence identity;

(b) contacting the two or more DNA molecules to be assembled from step (a) with a thermolabile/heat labile 31-5' exonuclease that generates 5' single stranded overhangs at the terminal regions of the dsDNA molecules, wherein the 3'-5' exonuclease is a mutated DNA polymerase II (pol II) derived 31-5' exonuclease comprising an amino acid sequence which is at least 95% identical over the entire length of the sequence with SEQ ID NO: 11, wherein the amino acid sequence includes one or more of the following substitutions: i) D442 is A or a conservative substitution for A; ii) D568 is A or a conservative substitution for A; iii) D442 is E; iv) D568 is E; and/or v) S445 is R or a conservative substitution for R, wherein said 3'-5' exonuclease is without polymerase activity and wherein said enzyme is irreversibly inactivated at temperatures above 30° C.;

(c) incubating the DNA molecules generated in step (b) under conditions whereby the overlapping overhanging regions of the two or more DNA molecules anneal; and (d) contacting the annealed assembled DNA molecules of step (c) with a thermolabile/heat labile DNA polymerase I (pol I) under conditions whereby the remining single-stranded gaps between the annealed fragments are filled in by the pol I enzyme thereby assembling the two or more dsDNA molecules, wherein the DNA pol I comprises an amino acid sequence which is at least 95% identical over the entire length of the sequence with SEQ ID NO: 2, wherein the amino acid sequence includes one or more of the following substitutions or combinations of substitutions: i) A450 is D or a conservative substitution for D, ii) R521 is A or a conservative substitution for A, iii) A450 is D or a conservative substitution for D, and F451 is A or a conservative substitution for A, iv) S449 is A or a conservative substitution for A, and F451 is A or a conservative substitution for A, v) S449 is A or a conservative substitution for A, and A450 is D or a conservative substitution for D, and/or vi) S449 is A or a conservative substitution for A, A450 is D or a conservative substitution for D, and R521 is A or a conservative substitution for A, and wherein the DNA pol I is irreversibly inactivated at temperatures above 30° C. and is without strand displacement activity.

2. The process according to claim 1, wherein the process takes place at a temperature from about 18° C. to about 25° C.

3. The process according to claim 1, wherein the single stranded overhangs generated in step (b) are at least 8 bases long.

4. The process according to claim 1, wherein the 31-5' exonuclease enzyme of step (b) exhibits exonuclease activity in the presence of dNTPs.

5. The process according to claim 1, wherein the DNA pol I enzyme is a DNA pol I enzyme having 3'-5' exonuclease activity.

6. The process according to claim 1, wherein the 3'-5' exonuclease is derived from the bacterium *Moritella viscosa*.

7. The process according to claim 6, wherein the 31-5' exonuclease comprises an amino acid sequence selected from the group consisting of SEQ ID No. 12, SEQ ID No. 13, SEQ ID No. 14, SEQ ID No. 15, SEQ ID No. 16 and SEQ ID No. 17.

8. The process according to claim 1, wherein the DNA pol I comprises an amino acid sequence selected from the group consisting of SEQ ID No. 3, SEQ ID No. 4, SEQ ID No. 5, SEQ ID No. 6, SEQ ID No. 7 and SEQ ID No. 8.

9. The process according to claim 1, wherein the DNA pol I is a large fragment DNA pol I.

10. A kit comprising:
(a) a first container comprising a DNA pol II derived 3'-5'exonuclease, wherein the 3'-5' exonuclease is a mutated DNA polymerase II (pol II) derived 31-5' exonuclease comprising an amino acid sequence which is at least 95% identical over the entire length of the sequence with SEQ ID NO: 11, wherein the amino acid sequence includes one or more of the following substitutions: i) D442 is A or a conservative substitution for A; ii) D568 is A or a conservative substitution for A; iii) D442 is E; iv) D568 is E; and/or v) S445 is R or a conservative substitution for R, wherein said 3'-5' exonuclease is without polymerase activity and wherein said enzyme is irreversibly inactivated at temperatures above 30° C., wherein said DNA exonuclease is without polymerase activity, and wherein said exonuclease activity is irreversibly inactivated at temperatures above 30° C.; and
(b) a second container comprising a DNA pol I, wherein the DNA pol I comprises an amino acid sequence which is at least 95% identical over the entire length of the sequence with SEQ ID NO: 2, wherein the amino acid sequence includes one or more of the following substitutions or combinations of substitutions: i) A450 is D or a conservative substitution for D, ii) R521 is A or a conservative substitution for A, iii) A450 is D or a conservative substitution for D, and F451 is A or a conservative substitution for A, iv) S449 is A or a conservative substitution for A, and F451 is A or a conservative substitution for A, v) S449 is A or a conservative substitution for A, and A450 is D or a conservative substitution for D, and/or vi) S449 is A or a conservative substitution for A, A450 is D or a conservative substitution for D, and R521 is A or a conservative substitution for A, wherein said DNA Pol I is without strand-displacement activity and wherein said DNA pol I is irreversibly inactivated at temperatures above 30° C.

11. The kit according to claim 10, wherein the DNA pol II derived 31-5'exonuclease of the first container exhibits 3'-5' exonuclease activity in the presence of dNTPs and the DNA pol I of the second container has 31-5' exonuclease activity.

12. The kit according to claim 10, wherein the 3'-5'exonuclease of the first container comprises an amino acid sequences selected from the group consisting of SEQ ID NO: 12, SEQ ID No. 13, SEQ ID No. 14, SEQ ID No. 15, SEQ ID No. 16 and SEQ ID No. 17, and wherein the DNA pol I of the second container comprises an amino acid sequence selected from the group consisting of SEQ ID No. 3, SEQ ID No. 4, SEQ ID No. 5, SEQ ID No. 6, SEQ ID No. 7 and SEQ ID No. 8.

13. The kit according to claim 10, wherein the DNA pol I is a large fragment DNA pol I.

* * * * *

```
                                 SEQUENCE LISTING

<160> NUMBER OF SEQ ID NOS: 26

<210> SEQ ID NO 1
<211> LENGTH: 611
<212> TYPE: PRT
<213> ORGANISM: Artificial Sequence
<220> FEATURE:
<223> OTHER INFORMATION: Marine large fragment DNA polymerase I with
      variable amino acid positions
<220> FEATURE:
<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (521)..(521)
<223> OTHER INFORMATION: Xaa can be any naturally occurring amino acid

<400> SEQUENCE: 1

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
                20                  25                  30

Glu Thr Asp Ser Leu Asp Ser Ala Ala Ala Asn Leu Val Gly Val Cys
            35                  40                  45

Leu Ala Val Ala Asp Asn Glu Ala Cys Tyr Ile Pro Leu Gly His Thr
        50                  55                  60

Gly Gly Gly Asp Leu Leu Gly Asp Gly Ala Pro Glu Gln Ile Pro Met
65                  70                  75                  80
```

```
Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
            115                 120                 125

Ala Leu Ser Cys Gly Leu His Ser His Gly Met Asp Asn Leu Ser Glu
        130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
            165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
            195                 200                 205

Leu Glu Arg Gly Met Pro Ser Val Leu Ala Met Met Glu Asn Asn Gly
        210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
            245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
            275                 280                 285

Thr Gly Ala Gly Ile Leu Glu Ala Leu Glu His Val His Pro Leu Pro
        290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
            325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
            355                 360                 365

Ile Arg Thr Ala Phe Ile Ala Glu Pro Gly Asn Ile Leu Val Ala Ala
        370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
            405                 410                 415

Thr Ala Ser Glu Met Phe Gly Val Pro Ile Asp Gly Met Asp Ser Ser
            420                 425                 430

Val Arg Arg Ala Lys Ala Ile Asn Phe Gly Ile Ile Tyr Gly Ile
            435                 440                 445

Xaa Xaa Xaa Gly Leu Ala Asn Asn Leu Gly Ile Ser Arg Thr Glu Ala
        450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
            485                 490                 495

Thr Ile Phe Gly Arg Lys Cys His Ile Lys Gly Ile Asn Asp Lys Asn
```

-continued

```
                 500                 505                 510

Gly Ala Met Arg Gly Phe Gly Glu Xaa Gln Ala Ile Asn Ala Pro Ile
            515                 520                 525

Gln Gly Ala Ala Ala Asp Ile Met Arg Arg Ala Met Ile Arg Met Pro
        530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610

<210> SEQ ID NO 2
<211> LENGTH: 611
<212> TYPE: PRT
<213> ORGANISM: Artificial Sequence
<220> FEATURE:
<223> OTHER INFORMATION: Wild type sequence of marine large fragment DNA
      polymerase I

<400> SEQUENCE: 2

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
        180                 185                 190

Leu Lys Pro Arg Leu Ala Ser Glu Asn Val Ala Ser Val Tyr Glu Thr
    195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240
```

-continued

```
Gln Lys Lys Ala Gly Leu Glu Ala Glu Ala His Glu Leu Ala Gly Arg
            245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
            275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
            325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
            355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
            405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
            435                 440                 445

Ser Ala Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
            485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
            515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
            565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
            595                 600                 605

Asp Ala His
    610
```

<210> SEQ ID NO 3
<211> LENGTH: 611
<212> TYPE: PRT
<213> ORGANISM: Artificial Sequence
<220> FEATURE:
<223> OTHER INFORMATION: Marine large fragment DNA polymerase I modified -continued by mutagenesis

<400> SEQUENCE: 3

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
                20                  25                  30

Glu Thr Asp Ser Leu Asp Ser Ala Ala Ala Asn Leu Val Gly Val Cys
            35                  40                  45

Leu Ala Val Ala Asp Asn Glu Ala Cys Tyr Ile Pro Leu Gly His Thr
        50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
            115                 120                 125

Ala Leu Ser Cys Gly Leu His Ser His Gly Met Asp Asn Leu Ser Glu
        130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
            195                 200                 205

Leu Glu Arg Gly Met Pro Ser Val Leu Ala Met Met Glu Asn Asn Gly
        210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
            325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
            355                 360                 365

Ile Arg Thr Ala Phe Ile Ala Glu Pro Gly Asn Ile Leu Val Ala Ala
        370                 375                 380

Asp Tyr Ser Gln Val Glu Leu Arg Ile Leu Ala His Val Ala Asp Leu
385                 390                 395                 400

-continued

```
Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ser Asp Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
            515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
                580                 585                 590

Leu Ser Val Pro Leu Val Val Asp Ala Lys Ala Ala His Asn Trp Asn
            595                 600                 605

Asp Ala His
    610

<210> SEQ ID NO 4
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 4

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140
```

-continued

```
Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
            195                 200                 205

Leu Glu Arg Gly Met Pro Ser Val Leu Ala Met Met Glu Asn Asn Gly
        210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
            325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
            355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
            405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ala Ala Ala Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
            485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560
```

-continued

```
Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610
```

<210> SEQ ID NO 5
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 5

```
Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
            85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
            165                 170                 175

Pro Tyr Ala Ala Glu Asp Ala Asp Val Thr Leu Arg Leu Trp Lys Leu
        180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
            245                 250                 255

Ser Phe Asn Leu Gly Ser Pro Lys Gln Leu Gly Glu Ile Leu Phe Asp
        260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300
```

-continued

```
Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ala Asp Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610
```

```
<210> SEQ ID NO 6
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 6

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
                20                  25                  30

Glu Thr Asp Ser Leu Asp Ser Ala Ala Ala Asn Leu Val Gly Val Cys
```

-continued

```
            35                  40                  45
Leu Ala Val Ala Asp Asn Glu Ala Cys Tyr Ile Pro Leu Gly His Thr
    50                  55                  60
Gly Gly Gly Asp Leu Leu Gly Asp Gly Ala Pro Glu Gln Ile Pro Met
65                  70                  75                  80
Gln Thr Ala Leu Asp Val Leu Glu Pro Met Leu His Asn Ala Ala Val
                85                  90                  95
Leu Lys Ile Gly Gln Asn Phe Lys Tyr Asp Leu Gly Val Phe Gln Arg
            100                 105                 110
Tyr Gly Leu Gln Pro Ala Pro Tyr Asp Asp Thr Met Leu Ile Ser Tyr
            115                 120                 125
Ala Leu Ser Cys Gly Leu His Ser His Gly Met Asp Asn Leu Ser Glu
    130                 135                 140
Met Tyr Phe Asp His Lys Pro Ile Pro Phe Lys Glu Leu Val Gly Ser
145                 150                 155                 160
Gly Lys Ser Gln Lys Thr Phe Asn Gln Leu Ser Leu Glu Glu Ser Thr
            165                 170                 175
Pro Tyr Ala Ala Glu Asp Ala Asp Val Thr Leu Arg Leu Trp Lys Leu
            180                 185                 190
Leu Lys Pro Arg Leu Ala Ser Glu Asn Val Ala Ser Val Tyr Glu Thr
            195                 200                 205
Leu Glu Arg Gly Met Pro Ser Val Leu Ala Met Met Glu Asn Asn Gly
    210                 215                 220
Ile Lys Val Asp Lys Ala Val Leu Ala Arg Leu Ser Gly Asp Phe Glu
225                 230                 235                 240
Gln Lys Lys Ala Gly Leu Glu Ala Glu Ala His Glu Leu Ala Gly Arg
            245                 250                 255
Ser Phe Asn Leu Gly Ser Pro Lys Gln Leu Gly Glu Ile Leu Phe Asp
            260                 265                 270
Glu Leu Gly Leu Ser Gly Gly Lys Lys Thr Lys Thr Gly Ala Trp Gln
            275                 280                 285
Thr Gly Ala Gly Ile Leu Glu Ala Leu Glu His Val His Pro Leu Pro
    290                 295                 300
Lys Ala Ile Leu Glu Trp Arg His Tyr Ala Lys Leu Lys Ser Thr Tyr
305                 310                 315                 320
Thr Asp Thr Leu Pro Gln Gln Ile Asn Ala Arg Thr Gly Arg Val His
            325                 330                 335
Thr Ser Tyr Ser Leu Ala Ser Thr Ser Thr Gly Arg Leu Ser Ser Ser
            340                 345                 350
Asp Pro Asn Leu Gln Asn Ile Pro Ile Arg Thr Glu Asp Gly Arg Lys
            355                 360                 365
Ile Arg Thr Ala Phe Ile Ala Glu Pro Gly Asn Ile Leu Val Ala Ala
    370                 375                 380
Asp Tyr Ser Gln Val Glu Leu Arg Ile Leu Ala His Val Ala Asp Leu
385                 390                 395                 400
Thr Asn Met Lys Gln Ala Phe Ala Asp Gly Val Asp Ile His Ala Leu
                405                 410                 415
Thr Ala Ser Glu Met Phe Gly Val Pro Ile Asp Gly Met Asp Ser Ser
            420                 425                 430
Val Arg Arg Arg Ala Lys Ala Ile Asn Phe Gly Ile Ile Tyr Gly Ile
            435                 440                 445
Ser Asp Ala Gly Leu Ala Asn Asn Leu Gly Ile Ser Arg Thr Glu Ala
    450                 455                 460
```

-continued

```
Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
                500                 505                 510

Gly Ala Met Arg Gly Phe Gly Glu Arg Gln Ala Ile Asn Ala Pro Ile
                515                 520                 525

Gln Gly Ala Ala Ala Asp Ile Met Arg Arg Ala Met Ile Arg Met Pro
        530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
                580                 585                 590

Leu Ser Val Pro Leu Val Val Asp Ala Lys Ala Ala His Asn Trp Asn
        595                 600                 605

Asp Ala His
        610

<210> SEQ ID NO 7
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 7

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
                20                  25                  30

Glu Thr Asp Ser Leu Asp Ser Ala Ala Ala Asn Leu Val Gly Val Cys
            35                  40                  45

Leu Ala Val Ala Asp Asn Glu Ala Cys Tyr Ile Pro Leu Gly His Thr
        50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
                100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
        130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
        180                 185                 190

Leu Lys Pro Arg Leu Ala Ser Glu Asn Val Ala Ser Val Tyr Glu Thr
```

```
                195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
                260                 265                 270

Glu Leu Gly Leu Ser Gly Gly Lys Lys Thr Lys Thr Gly Ala Trp Gln
            275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
                340                 345                 350

Asp Pro Asn Leu Gln Asn Ile Pro Ile Arg Thr Glu Asp Gly Arg Lys
            355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
                420                 425                 430

Val Arg Arg Arg Ala Lys Ala Ile Asn Phe Gly Ile Ile Tyr Gly Ile
            435                 440                 445

Ala Asp Ala Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
                500                 505                 510

Gly Ala Met Arg Gly Phe Gly Glu Arg Gln Ala Ile Asn Ala Pro Ile
            515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
                580                 585                 590

Leu Ser Val Pro Leu Val Val Asp Ala Lys Ala Ala His Asn Trp Asn
            595                 600                 605

Asp Ala His
    610
```

-continued

<210> SEQ ID NO 8
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 8

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
        180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys

-continued

```
              355                360                365

Ile Arg Thr Ala Phe Ile Ala Glu Pro Gly Asn Ile Leu Val Ala Ala
    370                375                380

Asp Tyr Ser Gln Val Glu Leu Arg Ile Leu Ala His Val Ala Asp Leu
385                390                395                400

Thr Asn Met Lys Gln Ala Phe Ala Asp Gly Val Asp Ile His Ala Leu
                405                410                415

Thr Ala Ser Glu Met Phe Gly Val Pro Ile Asp Gly Met Asp Ser Ser
                420                425                430

Val Arg Arg Arg Ala Lys Ala Ile Asn Phe Gly Ile Ile Tyr Gly Ile
                435                440                445

Ser Ala Phe Gly Leu Ala Asn Asn Leu Gly Ile Ser Arg Thr Glu Ala
    450                455                460

Lys Glu Tyr Ile Asp Ser Tyr Phe Glu Lys Phe Pro Gly Ile Lys Thr
465                470                475                480

Tyr Met Glu Ser Ala Lys Asp Glu Ala Arg Glu Asn Gly Phe Val Lys
                485                490                495

Thr Ile Phe Gly Arg Lys Cys His Ile Lys Gly Ile Asn Asp Lys Asn
                500                505                510

Gly Ala Met Arg Gly Phe Gly Glu Ala Gln Ala Ile Asn Ala Pro Ile
                515                520                525

Gln Gly Ala Ala Ala Asp Ile Met Arg Arg Ala Met Ile Arg Met Pro
    530                535                540

Asn Ala Ile Ser Asn Ile Glu Asn Ala Arg Met Leu Leu Gln Val His
545                550                555                560

Asp Glu Leu Val Phe Glu Val Pro Glu Ala Ser Ala Glu Ala Leu Ile
                565                570                575

Lys Thr Val Lys Ser Val Met Gln Asn Ala Cys Ala Pro Ala Val His
                580                585                590

Leu Ser Val Pro Leu Val Val Asp Ala Lys Ala Ala His Asn Trp Asn
    595                600                605

Asp Ala His
    610
```

<210> SEQ ID NO 9
<211> LENGTH: 1836
<212> TYPE: DNA
<213> ORGANISM: Artificial Sequence
<220> FEATURE:
<223> OTHER INFORMATION: Marine large fragment DNA polymerase I, codon
      optimized

<400> SEQUENCE: 9

```
ttcgacaaaa gcaaatatga gtgcgttcag gatgttgaac gtctgcagca ttgggttgat      60
cgttgtaccg atgttggtta ttgtgcagtt gatctggaaa ccgatagcct ggatagcgca     120
gcagcaaatc tggttggtgt ttgtctggca gttgcagata atgaagcatg ttatattccg     180
ctgggtcata ccggtggtgg tgatctgctt ggtgatggtg caccggaaca aattccgatg     240
cagaccgcac tggatgttct ggaaccgatg ctgcataatg ccgcagttct gaaaattggc     300
cagaacttca atatgatct gggtgtgttt cagcgttatg gtctgcagcc tgcaccgtat     360
gatgatacca tgctgattag ctatgcactg agctgtggtc tgcatagcca tggtatggat     420
aatctgagcg aaatgtattt cgaccataaa ccgattccgt tcaaagaact ggttggtagc     480
ggtaaaagcc agaaaacctt taatcagctg agcctggaag aaagcacccc gtatgcagcc     540
```

-continued

```
gaagatgcag atgttaccct gcgtctgtgg aaactgctga aaccgcgtct ggcaagcgaa    600
aatgttgcaa gcgtttatga aaccctggaa cgtggtatgc cgagcgttct ggcaatgatg    660
gaaaataatg gtatcaaagt ggataaagcg gttctggcac gtctgagcgg tgattttgaa    720
cagaaaaaag caggtctgga agccgaagca catgaactgg caggtcgttc atttaatctg    780
ggtagcccga aacagctggg tgaaattctg tttgatgaac tgggtctgag tggtggcaaa    840
aaaaccaaaa ccggtgcatg gcagaccggt gcaggtattc tggaagcact ggaacatgtg    900
catccgctgc cgaaagcaat tctggaatgg cgtcattatg caaaactgaa aagcacctat    960
accgatacac tgccgcagca gattaatgca cgtaccggtc gtgttcatac cagctatagc    1020
ctggcaagca ccagcaccgg tcgtctgagc agcagcgatc cgaatctgca gaatattccg    1080
attcgtaccg aagatggtcg taaaattcgc accgcattta ttgcagaacc gggtaatatt    1140
ctggttgcag ccgattatag ccaggttgaa ctgcgtattc tggcacatgt tgcagatctg    1200
accaatatga acaggcatt tgcagatggt gttgatattc atgcactgac cgcaagtgaa    1260
atgtttggtg ttccgattga tggcatggat agcagcgttc gtcgtcgtgc aaaagcaatt    1320
aactttggta ttatctatgg catcagcgca tttggtctgg caaataatct gggcattagc    1380
cgcaccgaag caaaagaata tatcgatagc tacttcgaga agttccctgg cattaaaacc    1440
tatatggaaa gcgcaaaaga tgaagcccgt gaaaatggtt ttgtgaaaac gatttttggt    1500
cgcaagtgcc atattaaagg catcaacgat aaaaatggtg ccatgcgtgg ttttggtgaa    1560
cgtcaggcaa ttaacgcacc gattcagggt gcagcagcag atattatgcg tcgtgccatg    1620
attcgtatgc cgaatgccat tagcaatatt gaaaatgccc gtatgctgct tcaggttcat    1680
gatgagctgg tttttgaagt gccggaagca agcgcagaag cactgattaa aaccgttaaa    1740
agcgttatgc agaatgcatg tgcaccggca gttcatctga gcgttccgct ggttgttgat    1800
gcaaaagccg cacataattg gaatgatgcc cattaa                               1836
```

<210> SEQ ID NO 10
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease with variable amino acid positions
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (568)..(568)
<223> OTHER INFORMATION: Xaa can be any naturally occurring amino acid

<400> SEQUENCE: 10

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

-continued

```
Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
                100                 105                 110

Pro Pro Glu Arg Tyr Leu Met Glu Arg Phe Ile Lys Gly Ala Val Glu
            115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
                180                 185                 190

Pro Phe Lys Arg Val Tyr Met Ile Gly Glu Gln Pro Glu Arg Asp Leu
            195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
            275                 280                 285

Phe Leu Thr Leu His Gly Arg Val Val Val Asp Gly Ile Asp Ser Leu
    290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg
                325                 330                 335

Met Glu Gln Ile Asn His Asp Phe His Phe Asn Lys Val Lys Leu Ala
            340                 345                 350

Lys Tyr Asn Leu Gln Asp Cys Val Leu Val Trp Asp Ile Phe Val Lys
            355                 360                 365

Thr Arg Leu Leu Asp Phe Leu Leu Leu Arg Ser Gln Leu Thr Gly Leu
    370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
            420                 425                 430

Gly Leu Tyr Asp His Val Ile Val Leu Xaa Phe Lys Xaa Leu Tyr Pro
            435                 440                 445

Ser Ile Ile Arg Thr Phe Lys Ile Asp Pro Val Gly Leu Leu Glu Gly
    450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
```

-continued

```
                385             490             495
Gln Arg Asp Gln Ala Lys Leu Asp Lys Asp Ala Ala Arg Ser Gln Ala
            500             505             510
Ile Lys Ile Leu Met Asn Ser Phe Tyr Gly Val Leu Gly Ser Gly Gly
            515             520             525
Cys Arg Phe Tyr Asp Thr Arg Leu Ala Ser Ser Ile Thr Met Arg Gly
            530             535             540
Gln Glu Ile Met Gln Thr Thr Ala Lys Trp Ile Glu Glu Gln Gly Tyr
545             550             555             560
Lys Val Ile Tyr Gly Asp Thr Xaa Ser Thr Phe Val Leu Leu Asp Ala
            565             570             575
Ala Lys Phe Thr Glu Gly Asp Arg Ser Glu Gln Ala Asp Arg Met Gly
            580             585             590
Lys Glu Leu Ser Glu Tyr Ile Asn Gln Gln Trp Gln Arg His Leu Arg
            595             600             605
Glu Asp Tyr Asp Ile Asp Cys Phe Leu Asp Ile Glu Tyr Glu Val His
            610             615             620
Tyr His Lys Phe Leu Met Pro Thr Ile Arg Gly Leu Asp Lys Gly Ser
625             630             635             640
Lys Lys Arg Tyr Ala Gly Leu Val Asn Thr Lys Asp Gly Glu Lys Leu
            645             650             655
Ile Phe Lys Gly Leu Glu Thr Val Arg Thr Asp Trp Thr Asp Leu Ala
            660             665             670
Lys Met Phe Gln Met Glu Leu Tyr His Arg Val Phe His Gly Leu Ala
            675             680             685
Val Glu Asp Tyr Val Leu Glu Ile Val Glu Arg Thr Leu Ala Gly Glu
            690             695             700
Phe Asn Asp Lys Leu Val Tyr Arg Lys Arg Leu Arg Gln Glu Leu Ser
705             710             715             720
Ala Tyr Val Lys Asn Val Pro Pro His Val Lys Ala Ala Arg Ala Ala
            725             730             735
Asp Glu Lys Asn Arg Gln Leu Gly Gln Pro Leu Arg Tyr Gln His Lys
            740             745             750
Ala Trp Ile Ser Tyr Val Leu Thr Leu Ser Gly Pro Glu Ala Val Glu
            755             760             765
His Gln His Ser Val Leu Asp Phe Glu His Tyr Ile Glu Lys Gln Ile
            770             775             780
Lys Pro Ile Ala Asp Gly Ile Leu Pro Phe Ile Gly Leu Ser Phe Asp
785             790             795             800
Leu Ile Thr Asp Gln Gln Met Gly Leu Phe
            805             810
```

<210> SEQ ID NO 11
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, wild type sequence

<400> SEQUENCE: 11

```
Met Ser Ala Thr Tyr Leu Gly Phe Leu Leu Ser Arg His Ser Arg Asp
1               5               10              15
Arg Asn Gly Asn Asn Glu Leu Ser Tyr Trp Leu Ala Ser Glu Met Gly
            20              25              30
```

-continued

```
Ala Val Lys Leu Ile Pro Ala Thr Gln Gln Leu Val Met Phe Ile Pro
        35              40              45

Gln Asp Gln Leu Thr Thr Ala Leu Ala Cys Leu Ser Glu Leu Asn Pro
    50              55              60

Arg Phe Thr Phe Lys Asp Leu Lys Met Arg Ser Phe Asp Leu Glu Leu
65              70              75              80

Met Ser Ala Phe Tyr Phe Arg Thr Ser His Asp Phe His Arg Ala Gln
                85              90              95

Glu Leu Leu Arg Arg Lys Leu Val Thr Val Leu Glu Ala Asp Ile Arg
            100             105             110

Pro Pro Glu Arg Tyr Leu Met Glu Arg Phe Ile Lys Gly Ala Val Glu
        115             120             125

Phe Thr Gly Thr Pro Val Gln Arg Lys Gly Tyr Val Glu Phe Gln Gln
    130             135             140

Ala Gln Leu Lys Pro Ala Glu Leu Pro Asp Asn Leu Val Asp Lys Ile
145             150             155             160

Lys Gln Ile Ser Leu Asp Ile Glu Cys Ser Glu His Gly Glu Leu Tyr
                165             170             175

Ser Ile Gly Leu Tyr Ser Leu Ser Pro Ala Tyr Cys Pro Asp Gly Gln
            180             185             190

Pro Phe Lys Arg Val Tyr Met Ile Gly Glu Gln Pro Glu Arg Asp Leu
        195             200             205

Ala Gln Thr Pro Glu Ser Glu Pro Leu Ile His Trp Val Ala Asp Glu
    210             215             220

Lys Ser Leu Leu Leu Ala Leu Gln Ala Phe Ala Ile Ser Tyr Asp Pro
225             230             235             240

Asp Ile Phe Ile Gly Trp Asn Val Ile Asn Phe Asp Phe Arg Leu Leu
                245             250             255

Ala Gln Arg Ala Thr Phe His Asn Leu Lys Leu Ala Leu Gly Arg Gly
            260             265             270

Gly Gln Asn Leu His Trp Arg Asp Gly Arg Thr Pro Gln Gln Gln Gly
        275             280             285

Phe Leu Thr Leu His Gly Arg Val Val Val Asp Gly Ile Asp Ser Leu
    290             295             300

Lys Thr Ala Thr Tyr Ser Phe Pro Ser Phe Ser Leu Glu Asn Val Ala
305             310             315             320

Gln Glu Ile Leu Gly Val Gly Lys Asp Thr Asp Asp Val Asp Asn Arg
                325             330             335

Met Glu Gln Ile Asn His Asp Phe His Phe Asn Lys Val Lys Leu Ala
            340             345             350

Lys Tyr Asn Leu Gln Asp Cys Val Leu Val Trp Asp Ile Phe Val Lys
        355             360             365

Thr Arg Leu Leu Asp Phe Leu Leu Leu Arg Ser Gln Leu Thr Gly Leu
    370             375             380

Glu Leu Asp Arg Asn Gly Gly Ser Val Leu Ala Phe Thr Asn Val Tyr
385             390             395             400

Leu Pro Lys Leu His Arg Ala Gly Tyr Ile Ala Pro Asn Leu Arg Glu
                405             410             415

Ser Gly Val Met Ala Ser Pro Gly Gly Tyr Val Met Asp Ser Phe Pro
            420             425             430

Gly Leu Tyr Asp His Val Ile Val Leu Asp Phe Lys Ser Leu Tyr Pro
        435             440             445

Ser Ile Ile Arg Thr Phe Lys Ile Asp Pro Val Gly Leu Leu Glu Gly
```

```
            450              455              460

Val Gln Asn Pro Thr Glu Ala Ile Pro Gly Phe Arg Gly Gly Leu Phe
465              470              475              480

Asp Arg Glu Lys His Tyr Leu Pro Asp Ile Ile Thr Glu Leu Trp Ser
                 485              490              495

Gln Arg Asp Gln Ala Lys Leu Asp Lys Asp Ala Ala Arg Ser Gln Ala
                 500              505              510

Ile Lys Ile Leu Met Asn Ser Phe Tyr Gly Val Leu Gly Ser Gly Gly
                 515              520              525

Cys Arg Phe Tyr Asp Thr Arg Leu Ala Ser Ser Ile Thr Met Arg Gly
                 530              535              540

Gln Glu Ile Met Gln Thr Thr Ala Lys Trp Ile Glu Glu Gln Gly Tyr
545              550              555              560

Lys Val Ile Tyr Gly Asp Thr Asp Ser Thr Phe Val Leu Leu Asp Ala
                 565              570              575

Ala Lys Phe Thr Glu Gly Asp Arg Ser Glu Gln Ala Asp Arg Met Gly
                 580              585              590

Lys Glu Leu Ser Glu Tyr Ile Asn Gln Gln Trp Gln Arg His Leu Arg
                 595              600              605

Glu Asp Tyr Asp Ile Asp Cys Phe Leu Asp Ile Glu Tyr Glu Val His
                 610              615              620

Tyr His Lys Phe Leu Met Pro Thr Ile Arg Gly Leu Asp Lys Gly Ser
625              630              635              640

Lys Lys Arg Tyr Ala Gly Leu Val Asn Thr Lys Asp Gly Glu Lys Leu
                 645              650              655

Ile Phe Lys Gly Leu Glu Thr Val Arg Thr Asp Trp Thr Asp Leu Ala
                 660              665              670

Lys Met Phe Gln Met Glu Leu Tyr His Arg Val Phe His Gly Leu Ala
                 675              680              685

Val Glu Asp Tyr Val Leu Glu Ile Val Glu Arg Thr Leu Ala Gly Glu
                 690              695              700

Phe Asn Asp Lys Leu Val Tyr Arg Lys Arg Leu Arg Gln Glu Leu Ser
705              710              715              720

Ala Tyr Val Lys Asn Val Pro Pro His Val Lys Ala Ala Arg Ala Ala
                 725              730              735

Asp Glu Lys Asn Arg Gln Leu Gly Gln Pro Leu Arg Tyr Gln His Lys
                 740              745              750

Ala Trp Ile Ser Tyr Val Leu Thr Leu Ser Gly Pro Glu Ala Val Glu
                 755              760              765

His Gln His Ser Val Leu Asp Phe Glu His Tyr Ile Glu Lys Gln Ile
                 770              775              780

Lys Pro Ile Ala Asp Gly Ile Leu Pro Phe Ile Gly Leu Ser Phe Asp
785              790              795              800

Leu Ile Thr Asp Gln Gln Met Gly Leu Phe
                 805              810
```

```
<210> SEQ ID NO 12
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 12
```

```
Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
        50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
            115                 120                 125

Phe Thr Gly Thr Pro Val Gln Arg Lys Gly Tyr Val Glu Phe Gln Gln
        130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
            195                 200                 205

Ala Gln Thr Pro Glu Ser Glu Pro Leu Ile His Trp Val Ala Asp Glu
        210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
            275                 280                 285

Phe Leu Thr Leu His Gly Arg Val Val Val Asp Gly Ile Asp Ser Leu
        290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Val Asp Asn Arg
            325                 330                 335

Met Glu Gln Ile Asn His Asp Phe His Phe Asn Lys Val Lys Leu Ala
            340                 345                 350

Lys Tyr Asn Leu Gln Asp Cys Val Leu Val Trp Asp Ile Phe Val Lys
            355                 360                 365

Thr Arg Leu Leu Asp Phe Leu Leu Leu Arg Ser Gln Leu Thr Gly Leu
        370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
```

-continued

```
            420             425             430
Gly Leu Tyr Asp His Val Ile Val Leu Ala Phe Lys Ser Leu Tyr Pro
        435             440             445

Ser Ile Ile Arg Thr Phe Lys Ile Asp Pro Val Gly Leu Leu Glu Gly
        450             455             460

Val Gln Asn Pro Thr Glu Ala Ile Pro Gly Phe Arg Gly Gly Leu Phe
465             470             475             480

Asp Arg Glu Lys His Tyr Leu Pro Asp Ile Ile Thr Glu Leu Trp Ser
            485             490             495

Gln Arg Asp Gln Ala Lys Leu Asp Lys Asp Ala Ala Arg Ser Gln Ala
        500             505             510

Ile Lys Ile Leu Met Asn Ser Phe Tyr Gly Val Leu Gly Ser Gly Gly
        515             520             525

Cys Arg Phe Tyr Asp Thr Arg Leu Ala Ser Ser Ile Thr Met Arg Gly
        530             535             540

Gln Glu Ile Met Gln Thr Thr Ala Lys Trp Ile Glu Glu Gln Gly Tyr
545             550             555             560

Lys Val Ile Tyr Gly Asp Thr Asp Ser Thr Phe Val Leu Leu Asp Ala
            565             570             575

Ala Lys Phe Thr Glu Gly Asp Arg Ser Glu Gln Ala Asp Arg Met Gly
            580             585             590

Lys Glu Leu Ser Glu Tyr Ile Asn Gln Gln Trp Gln Arg His Leu Arg
            595             600             605

Glu Asp Tyr Asp Ile Asp Cys Phe Leu Asp Ile Glu Tyr Glu Val His
        610             615             620

Tyr His Lys Phe Leu Met Pro Thr Ile Arg Gly Leu Asp Lys Gly Ser
625             630             635             640

Lys Lys Arg Tyr Ala Gly Leu Val Asn Thr Lys Asp Gly Glu Lys Leu
            645             650             655

Ile Phe Lys Gly Leu Glu Thr Val Arg Thr Asp Trp Thr Asp Leu Ala
            660             665             670

Lys Met Phe Gln Met Glu Leu Tyr His Arg Val Phe His Gly Leu Ala
            675             680             685

Val Glu Asp Tyr Val Leu Glu Ile Val Glu Arg Thr Leu Ala Gly Glu
        690             695             700

Phe Asn Asp Lys Leu Val Tyr Arg Lys Arg Leu Arg Gln Glu Leu Ser
705             710             715             720

Ala Tyr Val Lys Asn Val Pro Pro His Val Lys Ala Ala Arg Ala Ala
            725             730             735

Asp Glu Lys Asn Arg Gln Leu Gly Gln Pro Leu Arg Tyr Gln His Lys
            740             745             750

Ala Trp Ile Ser Tyr Val Leu Thr Leu Ser Gly Pro Glu Ala Val Glu
            755             760             765

His Gln His Ser Val Leu Asp Phe Glu His Tyr Ile Glu Lys Gln Ile
        770             775             780

Lys Pro Ile Ala Asp Gly Ile Leu Pro Phe Ile Gly Leu Ser Phe Asp
785             790             795             800

Leu Ile Thr Asp Gln Gln Met Gly Leu Phe
            805             810

<210> SEQ ID NO 13
<211> LENGTH: 810
<212> TYPE: PRT
<213> ORGANISM: Artificial Sequence
```

-continued

<220> FEATURE:
<223> OTHER INFORMATION: Moritella viscosa DNA polymerase derived 3'-5'
     exonuclease, modified by mutagenesis

<400> SEQUENCE: 13

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
            245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
        275                 280                 285

Phe Leu Thr Leu His Gly Arg Val Val Val Asp Gly Ile Asp Ser Leu
    290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Val Asp Asn Arg
            325                 330                 335

Met Glu Gln Ile Asn His Asp Phe His Phe Asn Lys Val Lys Leu Ala
            340                 345                 350

Lys Tyr Asn Leu Gln Asp Cys Val Leu Val Trp Asp Ile Phe Val Lys
        355                 360                 365

Thr Arg Leu Leu Asp Phe Leu Leu Leu Arg Ser Gln Leu Thr Gly Leu
    370                 375                 380

Glu Leu Asp Arg Asn Gly Gly Ser Val Leu Ala Phe Thr Asn Val Tyr

-continued

```
385                390                395                400

Leu Pro Lys Leu His Arg Ala Gly Tyr Ile Ala Pro Asn Leu Arg Glu
            405                410                415

Ser Gly Val Met Ala Ser Pro Gly Gly Tyr Val Met Asp Ser Phe Pro
            420                425                430

Gly Leu Tyr Asp His Val Ile Val Leu Asp Phe Lys Ser Leu Tyr Pro
            435                440                445

Ser Ile Ile Arg Thr Phe Lys Ile Asp Pro Val Gly Leu Leu Glu Gly
    450                455                460

Val Gln Asn Pro Thr Glu Ala Ile Pro Gly Phe Arg Gly Gly Leu Phe
465                470                475                480

Asp Arg Glu Lys His Tyr Leu Pro Asp Ile Ile Thr Glu Leu Trp Ser
            485                490                495

Gln Arg Asp Gln Ala Lys Leu Asp Lys Asp Ala Ala Arg Ser Gln Ala
            500                505                510

Ile Lys Ile Leu Met Asn Ser Phe Tyr Gly Val Leu Gly Ser Gly Gly
            515                520                525

Cys Arg Phe Tyr Asp Thr Arg Leu Ala Ser Ser Ile Thr Met Arg Gly
    530                535                540

Gln Glu Ile Met Gln Thr Thr Ala Lys Trp Ile Glu Glu Gln Gly Tyr
545                550                555                560

Lys Val Ile Tyr Gly Asp Thr Ala Ser Thr Phe Val Leu Leu Asp Ala
            565                570                575

Ala Lys Phe Thr Glu Gly Asp Arg Ser Glu Gln Ala Asp Arg Met Gly
            580                585                590

Lys Glu Leu Ser Glu Tyr Ile Asn Gln Gln Trp Gln Arg His Leu Arg
            595                600                605

Glu Asp Tyr Asp Ile Asp Cys Phe Leu Asp Ile Glu Tyr Glu Val His
    610                615                620

Tyr His Lys Phe Leu Met Pro Thr Ile Arg Gly Leu Asp Lys Gly Ser
625                630                635                640

Lys Lys Arg Tyr Ala Gly Leu Val Asn Thr Lys Asp Gly Glu Lys Leu
            645                650                655

Ile Phe Lys Gly Leu Glu Thr Val Arg Thr Asp Trp Thr Asp Leu Ala
            660                665                670

Lys Met Phe Gln Met Glu Leu Tyr His Arg Val Phe His Gly Leu Ala
            675                680                685

Val Glu Asp Tyr Val Leu Glu Ile Val Glu Arg Thr Leu Ala Gly Glu
    690                695                700

Phe Asn Asp Lys Leu Val Tyr Arg Lys Arg Leu Arg Gln Glu Leu Ser
705                710                715                720

Ala Tyr Val Lys Asn Val Pro Pro His Val Lys Ala Ala Arg Ala Ala
            725                730                735

Asp Glu Lys Asn Arg Gln Leu Gly Gln Pro Leu Arg Tyr Gln His Lys
            740                745                750

Ala Trp Ile Ser Tyr Val Leu Thr Leu Ser Gly Pro Glu Ala Val Glu
            755                760                765

His Gln His Ser Val Leu Asp Phe Glu His Tyr Ile Glu Lys Gln Ile
            770                775                780

Lys Pro Ile Ala Asp Gly Ile Leu Pro Phe Ile Gly Leu Ser Phe Asp
785                790                795                800

Leu Ile Thr Asp Gln Gln Met Gly Leu Phe
            805                810
```

-continued

```
<210> SEQ ID NO 14
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 14

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
        275                 280                 285

Phe Leu Thr Leu His Gly Arg Val Val Val Asp Gly Ile Asp Ser Leu
    290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Val Asp Asn Arg
                325                 330                 335

Met Glu Gln Ile Asn His Asp Phe His Phe Asn Lys Val Lys Leu Ala
            340                 345                 350

Lys Tyr Asn Leu Gln Asp Cys Val Leu Val Trp Asp Ile Phe Val Lys
```

-continued

```
               355                 360                 365

Thr Arg Leu Leu Asp Phe Leu Leu Leu Arg Ser Gln Leu Thr Gly Leu
    370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
                420                 425                 430

Gly Leu Tyr Asp His Val Ile Val Leu Glu Phe Lys Ser Leu Tyr Pro
                435                 440                 445

Ser Ile Ile Arg Thr Phe Lys Ile Asp Pro Val Gly Leu Leu Glu Gly
        450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
                485                 490                 495

Gln Arg Asp Gln Ala Lys Leu Asp Lys Asp Ala Ala Arg Ser Gln Ala
                500                 505                 510

Ile Lys Ile Leu Met Asn Ser Phe Tyr Gly Val Leu Gly Ser Gly Gly
            515                 520                 525

Cys Arg Phe Tyr Asp Thr Arg Leu Ala Ser Ser Ile Thr Met Arg Gly
        530                 535                 540

Gln Glu Ile Met Gln Thr Thr Ala Lys Trp Ile Glu Glu Gln Gly Tyr
545                 550                 555                 560

Lys Val Ile Tyr Gly Asp Thr Asp Ser Thr Phe Val Leu Leu Asp Ala
                565                 570                 575

Ala Lys Phe Thr Glu Gly Asp Arg Ser Glu Gln Ala Asp Arg Met Gly
                580                 585                 590

Lys Glu Leu Ser Glu Tyr Ile Asn Gln Gln Trp Gln Arg His Leu Arg
                595                 600                 605

Glu Asp Tyr Asp Ile Asp Cys Phe Leu Asp Ile Glu Tyr Glu Val His
        610                 615                 620

Tyr His Lys Phe Leu Met Pro Thr Ile Arg Gly Leu Asp Lys Gly Ser
625                 630                 635                 640

Lys Lys Arg Tyr Ala Gly Leu Val Asn Thr Lys Asp Gly Glu Lys Leu
                645                 650                 655

Ile Phe Lys Gly Leu Glu Thr Val Arg Thr Asp Trp Thr Asp Leu Ala
                660                 665                 670

Lys Met Phe Gln Met Glu Leu Tyr His Arg Val Phe His Gly Leu Ala
                675                 680                 685

Val Glu Asp Tyr Val Leu Glu Ile Val Glu Arg Thr Leu Ala Gly Glu
            690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
                725                 730                 735

Asp Glu Lys Asn Arg Gln Leu Gly Gln Pro Leu Arg Tyr Gln His Lys
                740                 745                 750

Ala Trp Ile Ser Tyr Val Leu Thr Leu Ser Gly Pro Glu Ala Val Glu
            755                 760                 765

His Gln His Ser Val Leu Asp Phe Glu His Tyr Ile Glu Lys Gln Ile
        770                 775                 780
```

-continued

```
Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810

<210> SEQ ID NO 15
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 15

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
                20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
        50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
        275                 280                 285

Phe Leu Thr Leu His Gly Arg Val Val Val Asp Gly Ile Asp Ser Leu
    290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg
```

-continued

```
                      325                   330                   335

Met Glu Gln Ile Asn His Asp Phe His Phe Asn Lys Val Lys Leu Ala
                  340                   345                   350

Lys Tyr Asn Leu Gln Asp Cys Val Leu Val Trp Asp Ile Phe Val Lys
                  355                   360                   365

Thr Arg Leu Leu Asp Phe Leu Leu Leu Arg Ser Gln Leu Thr Gly Leu
          370                   375                   380

Glu Leu Asp Arg Asn Gly Gly Ser Val Leu Ala Phe Thr Asn Val Tyr
385                   390                   395                   400

Leu Pro Lys Leu His Arg Ala Gly Tyr Ile Ala Pro Asn Leu Arg Glu
                  405                   410                   415

Ser Gly Val Met Ala Ser Pro Gly Gly Tyr Val Met Asp Ser Phe Pro
                  420                   425                   430

Gly Leu Tyr Asp His Val Ile Val Leu Asp Phe Lys Ser Leu Tyr Pro
                  435                   440                   445

Ser Ile Ile Arg Thr Phe Lys Ile Asp Pro Val Gly Leu Leu Glu Gly
          450                   455                   460

Val Gln Asn Pro Thr Glu Ala Ile Pro Gly Phe Arg Gly Gly Leu Phe
465                   470                   475                   480

Asp Arg Glu Lys His Tyr Leu Pro Asp Ile Ile Thr Glu Leu Trp Ser
                  485                   490                   495

Gln Arg Asp Gln Ala Lys Leu Asp Lys Asp Ala Ala Arg Ser Gln Ala
                  500                   505                   510

Ile Lys Ile Leu Met Asn Ser Phe Tyr Gly Val Leu Gly Ser Gly Gly
                  515                   520                   525

Cys Arg Phe Tyr Asp Thr Arg Leu Ala Ser Ser Ile Thr Met Arg Gly
          530                   535                   540

Gln Glu Ile Met Gln Thr Thr Ala Lys Trp Ile Glu Glu Gln Gly Tyr
545                   550                   555                   560

Lys Val Ile Tyr Gly Asp Thr Glu Ser Thr Phe Val Leu Leu Asp Ala
                  565                   570                   575

Ala Lys Phe Thr Glu Gly Asp Arg Ser Glu Gln Ala Asp Arg Met Gly
                  580                   585                   590

Lys Glu Leu Ser Glu Tyr Ile Asn Gln Gln Trp Gln Arg His Leu Arg
                  595                   600                   605

Glu Asp Tyr Asp Ile Asp Cys Phe Leu Asp Ile Glu Tyr Glu Val His
          610                   615                   620

Tyr His Lys Phe Leu Met Pro Thr Ile Arg Gly Leu Asp Lys Gly Ser
625                   630                   635                   640

Lys Lys Arg Tyr Ala Gly Leu Val Asn Thr Lys Asp Gly Glu Lys Leu
                  645                   650                   655

Ile Phe Lys Gly Leu Glu Thr Val Arg Thr Asp Trp Thr Asp Leu Ala
                  660                   665                   670

Lys Met Phe Gln Met Glu Leu Tyr His Arg Val Phe His Gly Leu Ala
                  675                   680                   685

Val Glu Asp Tyr Val Leu Glu Ile Val Glu Arg Thr Leu Ala Gly Glu
          690                   695                   700

Phe Asn Asp Lys Leu Val Tyr Arg Lys Arg Leu Arg Gln Glu Leu Ser
705                   710                   715                   720

Ala Tyr Val Lys Asn Val Pro Pro His Val Lys Ala Ala Arg Ala Ala
                  725                   730                   735

Asp Glu Lys Asn Arg Gln Leu Gly Gln Pro Leu Arg Tyr Gln His Lys
                  740                   745                   750
```

```
Ala Trp Ile Ser Tyr Val Leu Thr Leu Ser Gly Pro Glu Ala Val Glu
        755             760             765

His Gln His Ser Val Leu Asp Phe Glu His Tyr Ile Glu Lys Gln Ile
    770             775             780

Lys Pro Ile Ala Asp Gly Ile Leu Pro Phe Ile Gly Leu Ser Phe Asp
785             790             795             800

Leu Ile Thr Asp Gln Gln Met Gly Leu Phe
                805             810

<210> SEQ ID NO 16
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 16

Met Ser Ala Thr Tyr Leu Gly Phe Leu Leu Ser Arg His Ser Arg Asp
1               5               10              15

Arg Asn Gly Asn Asn Glu Leu Ser Tyr Trp Leu Ala Ser Glu Met Gly
            20              25              30

Ala Val Lys Leu Ile Pro Ala Thr Gln Gln Leu Val Met Phe Ile Pro
        35              40              45

Gln Asp Gln Leu Thr Thr Ala Leu Ala Cys Leu Ser Glu Leu Asn Pro
    50              55              60

Arg Phe Thr Phe Lys Asp Leu Lys Met Arg Ser Phe Asp Leu Glu Leu
65              70              75              80

Met Ser Ala Phe Tyr Phe Arg Thr Ser His Asp Phe His Arg Ala Gln
                85              90              95

Glu Leu Leu Arg Arg Lys Leu Val Thr Val Leu Glu Ala Asp Ile Arg
            100             105             110

Pro Pro Glu Arg Tyr Leu Met Glu Arg Phe Ile Lys Gly Ala Val Glu
        115             120             125

Phe Thr Gly Thr Pro Val Gln Arg Lys Gly Tyr Val Glu Phe Gln Gln
    130             135             140

Ala Gln Leu Lys Pro Ala Glu Leu Pro Asp Asn Leu Val Asp Lys Ile
145             150             155             160

Lys Gln Ile Ser Leu Asp Ile Glu Cys Ser Glu His Gly Glu Leu Tyr
                165             170             175

Ser Ile Gly Leu Tyr Ser Leu Ser Pro Ala Tyr Cys Pro Asp Gly Gln
            180             185             190

Pro Phe Lys Arg Val Tyr Met Ile Gly Glu Gln Pro Glu Arg Asp Leu
        195             200             205

Ala Gln Thr Pro Glu Ser Glu Pro Leu Ile His Trp Val Ala Asp Glu
    210             215             220

Lys Ser Leu Leu Leu Ala Leu Gln Ala Phe Ala Ile Ser Tyr Asp Pro
225             230             235             240

Asp Ile Phe Ile Gly Trp Asn Val Ile Asn Phe Asp Phe Arg Leu Leu
                245             250             255

Ala Gln Arg Ala Thr Phe His Asn Leu Lys Leu Ala Leu Gly Arg Gly
            260             265             270

Gly Gln Asn Leu His Trp Arg Asp Gly Arg Thr Pro Gln Gln Gln Gly
        275             280             285

Phe Leu Thr Leu His Gly Arg Val Val Val Asp Gly Ile Asp Ser Leu
```

-continued

```
        290             295             300
Lys Thr Ala Thr Tyr Ser Phe Pro Ser Phe Ser Leu Glu Asn Val Ala
305             310             315             320

Gln Glu Ile Leu Gly Val Gly Lys Asp Thr Asp Asp Val Asp Asn Arg
            325             330             335

Met Glu Gln Ile Asn His Asp Phe His Phe Asn Lys Val Lys Leu Ala
            340             345             350

Lys Tyr Asn Leu Gln Asp Cys Val Leu Val Trp Asp Ile Phe Val Lys
            355             360             365

Thr Arg Leu Leu Asp Phe Leu Leu Leu Arg Ser Gln Leu Thr Gly Leu
            370             375             380

Glu Leu Asp Arg Asn Gly Gly Ser Val Leu Ala Phe Thr Asn Val Tyr
385             390             395             400

Leu Pro Lys Leu His Arg Ala Gly Tyr Ile Ala Pro Asn Leu Arg Glu
            405             410             415

Ser Gly Val Met Ala Ser Pro Gly Gly Tyr Val Met Asp Ser Phe Pro
            420             425             430

Gly Leu Tyr Asp His Val Ile Val Leu Ala Phe Lys Ser Leu Tyr Pro
            435             440             445

Ser Ile Ile Arg Thr Phe Lys Ile Asp Pro Val Gly Leu Leu Glu Gly
            450             455             460

Val Gln Asn Pro Thr Glu Ala Ile Pro Gly Phe Arg Gly Gly Leu Phe
465             470             475             480

Asp Arg Glu Lys His Tyr Leu Pro Asp Ile Ile Thr Glu Leu Trp Ser
            485             490             495

Gln Arg Asp Gln Ala Lys Leu Asp Lys Asp Ala Ala Arg Ser Gln Ala
            500             505             510

Ile Lys Ile Leu Met Asn Ser Phe Tyr Gly Val Leu Gly Ser Gly Gly
            515             520             525

Cys Arg Phe Tyr Asp Thr Arg Leu Ala Ser Ser Ile Thr Met Arg Gly
            530             535             540

Gln Glu Ile Met Gln Thr Thr Ala Lys Trp Ile Glu Glu Gln Gly Tyr
545             550             555             560

Lys Val Ile Tyr Gly Asp Thr Ala Ser Thr Phe Val Leu Leu Asp Ala
            565             570             575

Ala Lys Phe Thr Glu Gly Asp Arg Ser Glu Gln Ala Asp Arg Met Gly
            580             585             590

Lys Glu Leu Ser Glu Tyr Ile Asn Gln Gln Trp Gln Arg His Leu Arg
            595             600             605

Glu Asp Tyr Asp Ile Asp Cys Phe Leu Asp Ile Glu Tyr Glu Val His
            610             615             620

Tyr His Lys Phe Leu Met Pro Thr Ile Arg Gly Leu Asp Lys Gly Ser
625             630             635             640

Lys Lys Arg Tyr Ala Gly Leu Val Asn Thr Lys Asp Gly Glu Lys Leu
            645             650             655

Ile Phe Lys Gly Leu Glu Thr Val Arg Thr Asp Trp Thr Asp Leu Ala
            660             665             670

Lys Met Phe Gln Met Glu Leu Tyr His Arg Val Phe His Gly Leu Ala
            675             680             685

Val Glu Asp Tyr Val Leu Glu Ile Val Glu Arg Thr Leu Ala Gly Glu
            690             695             700

Phe Asn Asp Lys Leu Val Tyr Arg Lys Arg Leu Arg Gln Glu Leu Ser
705             710             715             720
```

-continued

```
Ala Tyr Val Lys Asn Val Pro Pro His Val Lys Ala Ala Arg Ala Ala
            725                 730                 735

Asp Glu Lys Asn Arg Gln Leu Gly Gln Pro Leu Arg Tyr Gln His Lys
            740                 745                 750

Ala Trp Ile Ser Tyr Val Leu Thr Leu Ser Gly Pro Glu Ala Val Glu
        755                 760                 765

His Gln His Ser Val Leu Asp Phe Glu His Tyr Ile Glu Lys Gln Ile
    770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810

<210> SEQ ID NO 17
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 17

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
                180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
```

-continued

```
            260             265             270
Gly Gln Asn Leu His Trp Arg Asp Gly Arg Thr Pro Gln Gln Gln Gly
        275             280             285
Phe Leu Thr Leu His Gly Arg Val Val Val Asp Gly Ile Asp Ser Leu
    290             295             300
Lys Thr Ala Thr Tyr Ser Phe Pro Ser Phe Ser Leu Glu Asn Val Ala
305             310             315             320
Gln Glu Ile Leu Gly Val Gly Lys Asp Thr Asp Asp Val Asp Asn Arg
            325             330             335
Met Glu Gln Ile Asn His Asp Phe His Phe Asn Lys Val Lys Leu Ala
            340             345             350
Lys Tyr Asn Leu Gln Asp Cys Val Leu Val Trp Asp Ile Phe Val Lys
        355             360             365
Thr Arg Leu Leu Asp Phe Leu Leu Leu Arg Ser Gln Leu Thr Gly Leu
        370             375             380
Glu Leu Asp Arg Asn Gly Gly Ser Val Leu Ala Phe Thr Asn Val Tyr
385             390             395             400
Leu Pro Lys Leu His Arg Ala Gly Tyr Ile Ala Pro Asn Leu Arg Glu
            405             410             415
Ser Gly Val Met Ala Ser Pro Gly Gly Tyr Val Met Asp Ser Phe Pro
            420             425             430
Gly Leu Tyr Asp His Val Ile Val Leu Asp Phe Lys Arg Leu Tyr Pro
            435             440             445
Ser Ile Ile Arg Thr Phe Lys Ile Asp Pro Val Gly Leu Leu Glu Gly
        450             455             460
Val Gln Asn Pro Thr Glu Ala Ile Pro Gly Phe Arg Gly Gly Leu Phe
465             470             475             480
Asp Arg Glu Lys His Tyr Leu Pro Asp Ile Ile Thr Glu Leu Trp Ser
            485             490             495
Gln Arg Asp Gln Ala Lys Leu Asp Lys Asp Ala Ala Arg Ser Gln Ala
            500             505             510
Ile Lys Ile Leu Met Asn Ser Phe Tyr Gly Val Leu Gly Ser Gly Gly
        515             520             525
Cys Arg Phe Tyr Asp Thr Arg Leu Ala Ser Ser Ile Thr Met Arg Gly
        530             535             540
Gln Glu Ile Met Gln Thr Thr Ala Lys Trp Ile Glu Glu Gln Gly Tyr
545             550             555             560
Lys Val Ile Tyr Gly Asp Thr Asp Ser Thr Phe Val Leu Leu Asp Ala
            565             570             575
Ala Lys Phe Thr Glu Gly Asp Arg Ser Glu Gln Ala Asp Arg Met Gly
            580             585             590
Lys Glu Leu Ser Glu Tyr Ile Asn Gln Gln Trp Gln Arg His Leu Arg
        595             600             605
Glu Asp Tyr Asp Ile Asp Cys Phe Leu Asp Ile Glu Tyr Glu Val His
        610             615             620
Tyr His Lys Phe Leu Met Pro Thr Ile Arg Gly Leu Asp Lys Gly Ser
625             630             635             640
Lys Lys Arg Tyr Ala Gly Leu Val Asn Thr Lys Asp Gly Glu Lys Leu
            645             650             655
Ile Phe Lys Gly Leu Glu Thr Val Arg Thr Asp Trp Thr Asp Leu Ala
            660             665             670
Lys Met Phe Gln Met Glu Leu Tyr His Arg Val Phe His Gly Leu Ala
            675             680             685
```

-continued

```
Val Glu Asp Tyr Val Leu Glu Ile Val Glu Arg Thr Leu Ala Gly Glu
    690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
                725                 730                 735

Asp Glu Lys Asn Arg Gln Leu Gly Gln Pro Leu Arg Tyr Gln His Lys
                740                 745                 750

Ala Trp Ile Ser Tyr Val Leu Thr Leu Ser Gly Pro Glu Ala Val Glu
                755                 760                 765

His Gln His Ser Val Leu Asp Phe Glu His Tyr Ile Glu Lys Gln Ile
    770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810
```

```
<210> SEQ ID NO 18
<211> LENGTH: 2433
<212> TYPE: DNA
<213> ORGANISM: Artificial Sequence
<220> FEATURE:
<223> OTHER INFORMATION: Moritella viscosa DNA polymerase derived 3'-5'
      exonuclease, encoding wild type sequence

<400> SEQUENCE: 18
atgtctgcta catatctggg tttttttatta tcgcgccata gccgtgatcg taatggtaac      60
aatgaattaa gctactggtt agcatctgaa atgggtgcgg ttaaactgat cccggcaacc     120
cagcagctgg tgatgttcat tcctcaagat caacttacca ctgcattagc ttgtttaagt     180
gagttgaatc cgcgctttac ctttaaagac ttgaaaatgc gtagctttga tttagaactt     240
atgagcgcct tttatttccg tacttcccat gattttcacc gcgcacaaga gttattaaga     300
cgtaagctgg ttacggtatt agaagccgat attcgcccac ctgagcgtta cttaatggag     360
cgttttatca aaggcgcagt cgagttcact ggtacgcctg tacaacgtaa aggctatgtt     420
gaatttcaac aagcacagct taaaccagct gaactgccag ataacttagt cgataaaata     480
aaacagatct cactggatat cgaatgttca gaacacggag agctttactc tattggtttg     540
tattccctaa gccctgctta ttgcccagat ggtcagccct ttaaacgggt atacatgata     600
ggtgagcagc ctgagcgcga tttagcacaa actcctgaaa gcgagccgtt aatccattgg     660
gttgccgacg agaaaagttt attactggcg ctgcaagcat cgcgatcag ttacgatccc      720 gacatttttta ttggttggaa tgtaattaac tttgatttcc gtttattagc ccaacgtgcc     780
acattccata atcttaaatt agcattgggt cgaggtgggc aaaacctgca ttggcgagat     840
ggccgtaccc cacagcaaca aggctttctg actttacacg gtcgggtggt cgttgatggt     900
attgatagtt taaaaacggc aacttatagc ttcccaagtt ttagtttaga aaacgtggca     960
caagagattc tcggtgttgg taaagatact gatgatgtcg ataatcgcat ggaacagatt    1020
aaccacgact tcattttttaa caaggtaaaa ctggcgaaat acaacctgca agattgcgtc    1080
ttagtgtggg atattttttgt taaaacccgt ttgttagatt ttttattact acgctcgcag    1140
ttaaccggtt tagaactaga tcgtaacggt ggatcggtat ggcgtttac caatgtgtat     1200 cttcctaagt tacatcgcgc gggttatatc gcgccaaatc tgcgtgagag tggggtaatg    1260
gcaagtcctg gcggttatgt gatggattca tttcctggct tgtatgatca tgtcatcgta    1320
```

-continued

```
ctggatttta aaagtctgta tccgtcaatt attcgcacct ttaaaattga tccggtaggg    1380
ttgctagaag gggttcaaaa cccgactgag gcgattccgg gtttccgtgg tggtttgttt    1440
gatcgtgaaa agcattacct tcccgatatt attaccgaac tgtggtcgca gcgcgatcaa    1500
gccaaactcg ataaagatgc tgcccgttca caggccatta aaatcttaat gaattcgttt    1560
tatggtgtgt tagggtcggg cggttgtcgt ttttatgata ctcgtttagc ctcgtcgatc    1620
accatgcgtg ggcaagaaat catgcagact accgcaaaat ggatcgaaga gcagggatat    1680
aaggtgattt atggcgatac cgattccacc tttgtattac tcgatgccgc caagtttacc    1740
gagggtgatc gtagcgaaca agccgatcgc atgggcaaag agctgtcaga atatattaac    1800
cagcagtggc aacgacacct acgtgaagat tacgatatcg actgtttctt agatattgaa    1860
tacgaagtgc attatcacaa gtttttaatg ccgactatcc gtggcttgga taaaggcagt    1920
aaaaagcgct atgccggatt agtgaatacc aaagatggtg aaaaacttat ttttaaaggg    1980
ctggaaaccg tacgtaccga ttggactgac ttagccaaga tgttccaaat ggagttatac    2040
catcgggtat ttcatggctt agcagtcgaa gattatgtac tggaaattgt agaaaggacc    2100
ttagcgggtg agtttaacga taagttagtt tatcgtaagc gtttacgcca agaattgtct    2160
gcttatgtga agaacgtgcc gccacatgta aaagcggcgc gtgctgctga tgagaagaat    2220
cgccaattag ggcaaccgtt acgttatcag cataaagcgt ggatcagtta tgtgttaacc    2280
ctaagtggcc ctgaagctgt cgagcatcaa cattcggtac tcgattttga gcattacatt    2340
gaaaaacaaa ttaaacccat tgctgatggt atcttgcctt ttattggctt gagttttgat    2400
ttgataaccg atcaacaaat gggattattt taa                                 2433
```

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19

```
caccttgtct gctacatatc tgggt                                            25
```

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20

```
ttaaaataat cccatttgtt gatcggttat ca                                    32
```

<210> SEQ ID NO 21
<211> LENGTH: 82
<212> TYPE: DNA
<213> ORGANISM: Artificial Sequence
<220> FEATURE:
<223> OTHER INFORMATION: molecular beacon template

<400> SEQUENCE: 21

```
ggcccgtagg aggaaaggac atcttctagc atacgggccg tcaagttcat ggccagtcaa    60
gtcgtcagaa atttcgcacc ac                                              82
```

<210> SEQ ID NO 22

```
<211> LENGTH: 19
<212> TYPE: DNA
<213> ORGANISM: Artificial Sequence
<220> FEATURE:
<223> OTHER INFORMATION: primer

<400> SEQUENCE: 22
gtggtgcgaa atttctgac                                              19

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
tatccaccaa tactaccta cgatactttg tccactcaat                        40

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
ataggtggtt atgatgggat gctatgaaac aggtgagtta                       40

<210> SEQ ID NO 25
<211> LENGTH: 39
<212> TYPE: DNA
<213> ORGANISM: Artificial Sequence
<220> FEATURE:
<223> OTHER INFORMATION: primer

<400> SEQUENCE: 25
tatccaccaa tactaccctc gatactttgt ccactcaat                        39

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
ataggtggtt atgatgggat gctatgaaac aggtgagtta                       40
```